(12) United States Patent
Mougenot et al.

(10) Patent No.: US 9,420,989 B2
(45) Date of Patent: Aug. 23, 2016

(54) APPARATUS, METHOD AND COMPUTER PROGRAM PRODUCT FOR CALCULATING THE SPEED OF ULTRASOUND IN AT LEAST TWO TISSUE TYPES

(75) Inventors: Charles Mougenot, Toronto (CA); Gosta Jakob Ehnholm, Helsinki (FI); Iipo Asko Julius Koskela, Helsinkki (FI); Max Oskar Köhler, Espoo (FI)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/002,270

(22) PCT Filed: Feb. 27, 2012

(86) PCT No.: PCT/IB2012/050886
§ 371 (c)(1),
(2), (4) Date: Aug. 29, 2013

(87) PCT Pub. No.: WO2012/117328
PCT Pub. Date: Sep. 7, 2012

(65) Prior Publication Data
US 2013/0338485 A1 Dec. 19, 2013

(51) Int. Cl.
*A61B 8/00* (2006.01)
*A61B 8/08* (2006.01)
(Continued)

(52) U.S. Cl.
CPC .............. *A61B 8/08* (2013.01); *A61B 5/1075* (2013.01); *A61B 8/0825* (2013.01);
(Continued)

(58) Field of Classification Search
CPC ........ A61B 8/08; A61B 8/025; A61B 8/0858; A61B 8/406; A61B 8/4494; A61B 8/585; A61B 2562/0204; A61B 2562/046; A61B 5/055; A61B 5/1075; A61B 6/50; A61B 6/5247; A61N 2007/0078; A61N 2007/0095; A61N 7/02; G01H 5/00
See application file for complete search history.

(56) References Cited

U.S. PATENT DOCUMENTS 5,522,869 A 6/1996 Burdette
5,590,653 A 1/1997 Aida
(Continued)

FOREIGN PATENT DOCUMENTS

JP 2009034262 A 2/2009

OTHER PUBLICATIONS

Tosic, Ivana et al "Ultrasound Tomography with Learned Dictionaries", Acoustics Speech and Signal Processing, 2010 IEEE International Conference. pp. 5502-5505.
Furusawa H' Namba K' Thomasen S' Akiyama F' Bendet. Magnetic Resonance-Guided Focused Ultrasound Surgery of Breast Cancer: Reliability and Effectiveness. J Am Coll Surg. Jul. 2006; 203(1):54-63.
(Continued)

*Primary Examiner* — Ruth S Smith

(57) ABSTRACT

A medical apparatus including an ultrasound transmitter and receiver system for acquiring ultrasound data descriptive of the speed of ultrasound along at least two paths. The medical apparatus further includes a medical imaging system for acquiring medical image data and a memory containing instructions that causes the processor to acquire the medical image data. The instructions further cause the processor to acquire the ultrasound data. The instructions further cause the processor to segment the medical image data into at least two tissue types. The instructions further causes the processor to determine at least two distances corresponding to the at least two paths in the subject. The instructions further cause the processor to calculate the speed of ultrasound in the at least two tissue types.

13 Claims, 13 Drawing Sheets

(51) Int. Cl.
*A61B 5/107* (2006.01)
*A61N 7/02* (2006.01)
*G01H 5/00* (2006.01)
A61B 5/055 (2006.01)
A61B 6/00 (2006.01)
A61N 7/00 (2006.01)

(52) U.S. Cl.
CPC ............ *A61B 8/0858* (2013.01); *A61B 8/406* (2013.01); *A61B 8/4494* (2013.01); *A61N 7/02* (2013.01); *G01H 5/00* (2013.01); *A61B 5/055* (2013.01); *A61B 6/50* (2013.01); *A61B 6/5247* (2013.01); *A61B 8/585* (2013.01); *A61B 2562/0204* (2013.01); *A61B 2562/046* (2013.01); *A61N 2007/0078* (2013.01); *A61N 2007/0095* (2013.01)

(56) References Cited

U.S. PATENT DOCUMENTS

| | | | |
|---|---|---|---|
| 6,516,211 | B1 | 2/2003 | Acker |
| 7,112,173 | B1 | 9/2006 | Kantorovich |
| 8,801,615 | B2 * | 8/2014 | Fernandez et al. ............ 600/439 |
| 2004/0122323 | A1 | 6/2004 | Vortman |
| 2008/0132785 | A1 | 6/2008 | Piron |
| 2008/0177180 | A1 | 7/2008 | Azhari et al. |
| 2008/0275339 | A1 | 11/2008 | Thiemann |

OTHER PUBLICATIONS

Scherzinger Al, Belgam Ra, Carson Pl, Meyer Cr, Sutherland Jv, Bookstein Fl, Silver Tm. Assessment of ultrasonic computed tomography in symptomatic breast patients by discriminant analysis. Ultrasound Med Biol. 1989;15(1):21-8. [4] Madsen El, Zagzebski Ja, Frank Gr.

Madsen El, Zagzebski Ja, Frank Gr, Greenleaf Jf, Carson Pl. Anthropomorphic breast phantoms for assessing ultrasonic imaging system performance and for training ultrasonographers: part I. J Clin Ultrasound. Feb. 1982;10 (2):67-75.

Madsen El, Zagzebski Ja, Frank Gr, Greenleaf Jf, Carson Pl. Anthropomorphic breast phantoms for assessing ultrasonic imaging system performance and for training ultrasonographers: part II. J Clin Ultrasound. Mar. 1982;10 (3):91-100.

Glover Gh, Computerized time-of-flight ultrasonic tomography for breast examination.Ultrasound Med. Biol., 1977; 3:117-127.

McDannold N' Clement Gt' Black P' Jolesz F' Hynynen K. Transcranial magnetic resonance imaging-guided focused ultrasound surgery of brain tumors: initial findings in 3 patients. Neurosurgery. Feb. 2010;66(2):323-32.

Francis A. Duck 1990 "Physical properties of tissue—A Comprehensive Reference Book" Chapter 4 acoustic properties Academic Press.

Rajagopalan B, Greenleaf Jf, Thomas Pj, Johnson Sa and Bahan Rc. Variation of acoustic speed with temperature in various exised human tissues studied by ultrasound computerized tomography. Ultrasonic Tissue Characterization II M. Linzer 1979; 227-233.

* cited by examiner

APPARATUS, METHOD AND COMPUTER PROGRAM PRODUCT FOR CALCULATING THE SPEED OF ULTRASOUND IN AT LEAST TWO TISSUE TYPES

CROSS-REFERENCE TO PRIOR APPLICATIONS

This application is the U.S. National Phase application under 35 U.S.C. §371 of International Application No. PCT/IB2012/050886, filed on Feb. 27, 2012, which claims the benefit of European Patent Application No. 11156819.2, filed on Mar. 3, 2011. These applications are hereby incorporated by reference herein.

TECHNICAL FIELD

The invention relates to medical imaging, in particular to calculation of the velocity of ultrasound in tissue using ultrasound and medical imaging.

BACKGROUND OF THE INVENTION

Ultrasound from a focused ultrasonic transducer can be used to selectively treat regions within the interior of the body. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to kill regions of cancer cells selectively. This technique has been applied to the treatment of uterine fibroids, and has reduced the need for hysterectomy procedures. At lower powers or in pulsed mode, ultrasound can be used to selectively deliver genetic material or medicine to a region.

To perform ultrasonic therapy, a focused ultrasonic transducer can be used to focus the ultrasound on a particular treatment volume. The transducer is typically mounted within a medium, such as degassed water, that is able to transmit ultrasound. Actuators are then used to adjust the position of the ultrasonic transducer and thereby adjust the tissue region that is being treated.

The US-patent application US2004/0122323 shows a system for focusing ultrasonic energy through tissue and an imager for imaging the tissue region. Phase and amplitude correction factors are employed to focus the ultrasonic energy. The respective correction factors compensate for variations in the speed of sound of the tissue types within the tissue types. These correction factors are determined by analysing images and identifying tissue characteristics from the images.

SUMMARY OF THE INVENTION

The invention provides for a medical apparatus, a method, and a computer program product in the independent claims. Embodiments are given in the dependent claims.

During the treatment of breast cancer by High Intensity Focused Ultrasound (HIFU), the ultrasound wave travels across several media, such as subcutaneous fat and glandular tissue, characterized by ultrasound celerities 1451±36 m/s and 1538 m/s±22 m/s, respectively. Within the beam path, a variation of 1 cm thickness of those two tissue types induces a phase aberration of 210° which is sufficient to defocus the beam. HIFU treatment is frequently combined with Magnetic Resonance Imaging (MRI) to localize cancer, plan the treatment, and monitor the hyperthermia procedure.

Anatomical image provided by MRI or another imaging modality could be also used to process phase and amplitude aberration compensation based on apriority of tissue celerity and attenuation. However breast tissues celerity (an essential parameter to compute refocusing) is patient and age dependant. Embodiments of the invention may provide for an apparatus and/or a method of characterizing the celerity and the attenuation of tissue types before or during treatment by adding ultrasound emitters and receivers inside a medical imaging system. The ultrasound emitters and receivers are used to measure ultrasound propagation time and attenuation along few directions, whereas anatomical images provide characterization of each tissue types along those directions. The celerity and attenuation values are thus obtained by combining both data. Those tissues characterizations, obtained rapidly prior or during the hyperthermia, will improve beam refocusing for a better treatment efficiency and accuracy.

The treatment of breast cancer by MR guided HIFU has recently shown great potential to enter in clinical practice. However, widespread clinical acceptance is hampered by the considerable risk of undesired tissue damage to the thoracic cage, the heart and the lung which are located in the far field of the ultrasound beam. Embodiments of the invention may provide a way to circumvent these risks by using of a transducer design with lateral principal beam direction. In addition, the lower energy density in the near-field of the beam allows treating larger tumors without exceeding the safety limits for undesired temperature elevations of the subcutaneous tissue layer.

The quality of the focal point of large aperture transducer designs is much more sensitive to the influence of inhomogeneous propagation media. Since breast tissue is in acoustic terms a complex structure of glandular, fatty, and fibrous tissues which display variations of the acoustic propagation speed of up to 6%, the use of such designs may result typically in a poor beam.

Embodiments of the invention may provide for a correction function which reestablishes the beam quality. Similar problems have been encountered for the design of trans-cranial HIFU ablation systems, where high-resolution CT-imaging is used as a basis for the calculation of a correction function assuming similar tissues acoustic properties for all patients. Nevertheless, these methods are not directly transferable to breast tissues since they are optimized to characterize and correct aberrations due to the beam propagation through osseous tissue. In addition the use of multi-modalities (CT and MRI) induces issue related to systems availability, workflow duration and images registration. Therefore, the key to allow the use of large aperture transducer designs for the optimal non-invasive treatment of breast cancer with HIFU is an effective, non-invasive method to characterize the acoustic properties of breast tissue in a clinically relevant time-frame.

MR-imaging displays an excellent soft-tissue contrast and is thus able to map heterogeneous tissue structures with a high spatial resolution. The combination of this information with a predefine table of in-vivo celerity measurements of different breast tissue types could be used to process refocusing method. However this method is limited since celerity of subcutaneous fat, glandular tissue is patient and age dependant.

Time of flight ultrasonic tomography platform has been proposed to quantify the celerity of breast tissues. However the resulting measurement requires long scan time (9 min/s per slice for article) with a contrast and spatial resolution limited to ultrasound state-of art. Embodiments of the invention may allow tissue heterogeneity compensation for HIFU treatment more patient specific by combining means to characterize ultrasound tissues properties with one or several imaging modalities (other than ultrasound celerity measurement).

The ultrasound celerity as well as the ultrasound attenuation can be characterized using ultrasound emitters and receivers combined with anatomical images of the patient. Anatomical images could be obtained using one or combining several imaging modalities such as:

Magnetic resonance imaging (MRI)
Radiography
   Fluoroscopy
   Projectional radiographs (x-rays)
Nuclear medicine
   Scintigraphy
   SPECT
   Positron emission tomography (PET)
Photo acoustic imaging
Breast Thermography
Tomography
   Linear tomography
   Poly tomography
   Zonography
   Orthopantomography (OPT or OPG)
   Computed Tomography (CT)
   Computed Axial Tomography (CAT)
Ultrasonography The ultrasound emitters and receivers can measure the propagation delay and the attenuation across several tissues layers. In addition, another imaging modality can provide quantification of the following characteristics along the propagation direction of ultrasound:

the thickness of each of tissue layers.
the tissue density distribution
the temperature distribution The combination of ultrasound emitter and receiver measurements with another imaging modality can improve the evaluation of ultrasound celerity and attenuation for each tissue types on a patient specific basis necessary to process optimal refocusing.

With embodiments of the invention, tissue characterization may be processed during the patient screening stage, during the planning stage, or on the fly during the HIFU treatment without significant procedure delay. The acquisition of ultrasound echoes requires few milliseconds which is much less than the acquisition time of most of other medical imaging modalities. In addition, the acquisition of ultrasound echoes can be acquired simultaneously to the use of other imaging modalities, if each system is integrated into the same platform and if acquisition systems are designed to avoid interferences in between each others. Other way data could be also acquired separately in any order and combined together for processing step after acquisitions of all necessary data Since, for example, MRI images initially acquired to plan the treatment could be re-used to process aberration correction for the selected target region, the related acquisition duration might not be consider as an additional duration.

However there is a benefit to measuring anatomy (i.e. tissue thickness) and acquisition of ultrasound echoes simultaneously or successively during the same session: they are automatically in the same reference frame. If the measurement of the tissue thickness and the acquisition of echoes are measured separately during two different sessions, one needs to be completely certain of the patient position during both measurements in order to co-register the ultrasound echoes used to assess the time-of-flight and the anatomical information.

The treatment of breast cancer is a good application for embodiments of the invention since ultrasound emitters and receivers can be oriented toward each other for an easy characterization of breast tissues along straight lines. In addition the treatment of breast cancer with large aperture transducer is more sensitive to tissue aberration which makes this application even more essential.

A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'processor' as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. Many programs have their instructions performed by multiple processors that may be within the same computing device or which may even be distributed across multiple computing devices.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses a interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

'Medical image data' encompasses one, two or three dimensional data that has been acquired using a medical imaging system. A 'medical imaging system' as used herein encompasses a apparatus adapted for acquiring information about the physical structure of a patient and construct sets of one dimensional, two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. A Magnetic Resonance Imaging image is defined herein as being the reconstructed one, two or three dimensional visualization of anatomic data contained within the magnetic resonance imaging data. This visualization can be performed using a processor or a computer. A magnetic resonance image is an example medical image data.

'Ultrasound data' as used herein encompasses data descriptive of an ultrasound beam that is transmitted through an object. Ultrasound data may comprise any combination of the following, but is not limited to: time of transmission by a transmitter, frequency of emitted ultrasound, time of reception by a receiver, delay between transmission and reception, amplitude of transmission, amplitude of reflection, and measured amplitude of the ultrasound by the receiver. For instance the amplitude and delay of reflection may be of particular interest if the ultrasound is bounced or pinged off of bone or another hard tissue structure.

The 'speed of ultrasound' as used herein encompasses a quantity descriptive of the velocity that ultrasound propagates through a solid or liquid medium. The term speed of ultrasound is synonymous with: ultrasound celerity, speed of sound, sound velocity, sound speed, and ultrasound speed, and ultrasound velocity.

An 'ultrasound window' as used herein encompasses a window which is able to transmit ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical apparatus comprising an ultrasound transmitter and receiver system for acquiring ultrasound data. The ultrasound data is descriptive of the speed of ultrasound along at least two paths in the subject. The ultrasound transmitter emits ultrasound and the receiver system receives the ultrasound. For instance a pulse of ultrasound can be emitted by the ultrasound transmitter and then it is received by the ultrasound receiver. The amplitude and/or the delay of the received ultrasonic pulse can be determined by the ultrasound receiver.

The medical apparatus further comprises a medical imaging system for acquiring medical image data descriptive of the at least two paths in the subject. The medical apparatus further comprises a processor for controlling the medical apparatus. The medical apparatus further comprises a memory containing machine executable instructions.

Execution of the machine executable instructions causes the processor to acquire the medical image data using the medical imaging system. For instance the processor may send control signals to the medical imaging system which control it such that medical image data is acquired. Execution of the machine executable instructions further causes the processor to acquire the ultrasound data using the ultrasound transmitter and receiver system. The order in which the medical image data and the ultrasound data are acquired is not relevant. For instance the medical image data may be acquired first, the ultrasound data may be acquired first, or the medical image data and the ultrasound data may be acquired simultaneously.

Execution of the machine executable instructions further causes the processor to segment the medical image into at least two tissue types. The medical image data may be descriptive of the anatomy of a subject. At least two different types of tissue are identified or segmented in the medical image data. The medical image data may be segmented using standard segmentation algorithms. For instance landmarks in the anatomical data of the medical image data may be identified. In another example a deformable model is fit to the medical image data. Execution of the machine executable instructions further causes the processor to determine at least two distances in the subject each of the at least two paths in the subject. The at least two distances correspond to the different distance traveled in the at least two tissue types by ultrasound generated by the ultrasound transmitter and receiver system. Execution of the machine executable instructions further causes the processor to calculate the speed of ultrasound in each of the at least two tissue types in accordance with the ultrasound data and with the at least two distances for each of the at least two paths.

This embodiment is particularly advantageous because it may be used to accurately determine the velocity of sound or ultrasound within multiple tissue types of a subject. For instance, if a portion of a subject contains more than one type of tissue it may be anticipated that the velocity of sound in the different types of tissue is different. By accurately determining the velocity of ultrasound in different regions of tissue, ultrasound may be more accurately focused. This is particularly valuable when the beam path of the individual phased-array transducer elements are very different, as is the case for wide-aperture transducers. Ultrasound is emitted along multiple paths and then medical image data is used to determine how long and what distance the ultrasound travels in each of the different tissue types. The knowledge of these distances combined with a knowledge of how long it takes the ultrasound to traverse each paths allows the velocity of ultrasound to be calculated. For instance the ultrasound data may contain the delay between an ultrasound pulse being emitted by the ultrasound transmitter and it being received by the receiver.

The embodiment may also be advantageous because the velocity of ultrasound in tissue may have diagnostic value.

In another embodiment, the ultrasound transmitter and receiver system has a first coordinate system. The medical imaging system has a second coordinate system. The first coordinate system is registered to the second coordinate system. This is advantageous because the data acquire by the medical imaging system and the ultrasound transmitter and receiver system can be correlated. This allows the merging of data into one common coordinate system, which is necessary for accurate determination of the speed of sound.

In another embodiment the medical apparatus further comprises a high-intensity focused ultrasound system for sonicating a target zone within the subject. The high-intensity focused ultrasound system comprises an ultrasound transducer for generating ultrasonic energy. The ultrasound transducer comprises multiple ultrasound transducer elements. The phase of each of the multiple ultrasound transducer elements is controllable. For instance each of the ultrasound transducer elements may be driven by an alternating current power supply. The phase and/or amplitude of electrical power supplied to each of the multiple ultrasound transducer elements may be controllable.

Execution of the instructions further causes the processor to calculate a set of transducer element phases in accordance with the segmented medical image data and the speed of ultrasound in each of the at least two tissue types. For instance, if it is desired to sonicate a particular location this location may be identified in the segmented medical image data. A knowledge of the relationship between the position of the high-intensity focused ultrasound transducer and the speed of ultrasound to the two tissue types allows a proper phase for each of the set of transducer elements to be chosen such that the high-intensity focused ultrasound is properly focused. Without doing this the phase at the target zone may be affected by there being a variety of different ultrasound velocities in the different tissue types. This embodiment is particularly advantageous because it allows the focused ultrasound to be more accurately focused into the target zone.

In another embodiment the medical apparatus comprises a tank. The tank has an opening for receiving an ultrasonic conducting liquid and a portion of the subject. The tank may for instance be a vessel or container which may be filled with the ultrasonic conducting liquid. An ultrasonic conducting liquid as used herein encompasses any liquid which is adapted for transmitting ultrasonic energy. It may for instance be a gel, an oil, or water. The tank is partially filled with the ultrasonic conducting liquid and then a portion of the subject is stuck into the tank. The portion contains the target zone. The ultrasound transmitter and receiver system is adapted for transmitting and receiving ultrasound predominantly within a first plane through the tank. By predominantly it is meant that the ultrasound transmitters and receivers of the ultrasound transmitter and receiver system are arranged such that the ultrasound generated by the ultrasound transmitters is mostly traveling through the first plane. The majority of ultrasound is generated such that it travels through the first plane. The first plane is below the opening. The multiple ultrasound transducer elements are below a second plane wherein the second plane is below the first plane.

In another embodiment the ultrasound transducer is focused above the second plane. This embodiment is advantageous because the ultrasound transducers focus up and possibly at the top of or out of the tank.

In another embodiment the ultrasound transducer is focused below the second plane. In this embodiment the ultrasound data is acquired above the sonication region.

In another embodiment the at least two paths are through the subject.

In another embodiment execution of the instructions further causes the processor to acquire the baseline ultrasound data using the ultrasound transmitter and receiver system. The baseline ultrasound data is acquired along at least two baseline paths through the ultrasonic conducting liquid. The baseline ultrasound data comprises ultrasonic amplitude measurements. The ultrasonic data comprises ultrasonic amplitude measurements. Execution of the instructions further causes the processor to calculate an attenuation value for each of the at least two tissue types. The attenuation value is calculated in accordance with the ultrasonic amplitude measurements of the ultrasonic data and the baseline ultrasound data in accordance with the at least two distances for each of the at least two paths. Using this information the attenuation in each tissue type can be calculated.

In another embodiment the medical apparatus further comprises a positioning system for positioning the subject and/or the ultrasound transmitter and receiver system. Execution of the instructions further causes the processor to identify bone tissue in the segmented medical image data. Execution of the instructions further causes the processor to position the subject and/or the ultrasound transmitter and receiver system such that the at least two paths are reflected off the bone tissue and received by the receiver system. For instance the processor may be connected to a mechanical actuating system that actuates the position of the ultrasound transmitter and receiver system. Alternatively the processor may be able to control a patient positioning system which is able to control the position of the subject. In this embodiment the ultrasound enters the subject and is reflected by bone. For instance in such an embodiment the transmitter and receiver may be positioned relative to an ultrasonic window that the subject is in contact with. This embodiment may be very advantageous because velocity of ultrasound through tissue and/or the attenuation of ultrasound in tissue can be determined near regions of subject through which ultrasound is not able to pass. For instance it would be difficult to pass a beam of ultrasound through a ribcage.

In another embodiment execution of the instructions further causes the processor to calculate the ultrasound attenuation in each of the at least two tissue types in accordance with the at least two distances for each of the at least two paths.

In another embodiment execution of the instructions further causes the processor to generate ultrasound control signals in accordance with the set of transducer element phases. As used herein the ultrasound control signals are commands and/or signals which are able to control the high-intensity focused ultrasound system. The ultrasound control signals causes the high-intensity focused ultrasound system to sonicate the target zone. Execution of the instructions further causes the processor to send the ultrasonic control signals to the high-intensity focused ultrasound system.

In another embodiment the medical imaging system is a magnetic resonance imaging system for acquiring magnetic resonance data from an imaging zone. The target zone is within the imaging zone. Execution of the instructions further causes the processor to acquire magnetic resonance thermometry data along a path generated from the ultrasound transducer to the target zone. Execution of the instructions further causes the processor to calculate a set of temperature compensated transducer element phases in accordance with the segmented medical image data and the magnetic resonance thermometry data.

Execution of the instructions further causes the processor to generate temperature corrected ultrasound control signals in accordance with the set of transducer element phases. Execution of the instructions further causes the processor to send the temperature corrected ultrasound control signals to the high-intensity focused ultrasound system. This embodiment is particularly advantageous because the velocity of ultrasound through the at least two tissue types may be temperature compensated. The temperature of body tissues stays relatively constant, however when heating the target zone using a high-intensity focused ultrasound system regions or hotspots may develop. In addition the sonication point within the target zone may also heat and change the velocity of ultrasound. This may cause slight defocusing. Heating in the near field of the ultrasound transducer may also cause defocusing.

In another embodiment the medical imaging system is a magnetic resonance imaging system. In this embodiment the medical image data may be a set of magnetic resonance image data. The magnetic resonance imaging system may acquire magnetic resonance data and then reconstruct it into the magnetic resonance image data.

In another embodiment the medical imaging system is a computer tomography system.

In another embodiment the medical imaging system is a diagnostic ultrasound system.

In another embodiment the at least two paths is a plurality or a large number of paths through the subject. Statistical methods may then be used to accurately determine the amplitude and/or velocity of ultrasound through the at least two tissue types in the subject.

In another aspect the invention provides for a method of operating a medical apparatus. The method may also provide for a computer-implemented method. The medical apparatus comprises an ultrasound transmitter and receiver system for acquiring ultrasound data. The ultrasound data is descriptive of the speed of ultrasound along at least two paths in the subject. The medical apparatus further comprises a medical imaging system for acquiring medical image data descriptive of the at least two paths in the subject. The method comprises the step of acquiring the medical image data using the medical imaging system. The method further comprises the step of acquiring the ultrasound data using the ultrasound transmitter and receiver system. The method further comprises the step of segmenting the medical image data into at least two tissue types. The method further comprises the step of determining at least two distances in the subject for each of the at least two paths in the subject by the ultrasound. The at least two distances correspond to the distance traveled in the at least two tissue types by ultrasound generated by the ultrasound transmitter and receiver system. The method further comprises the step of calculating the speed of ultrasound in each of the at least two tissue types in accordance with the ultrasound data and with the at least two distances for each of the at least two paths.

The medical apparatus further comprises a high-intensity focused ultrasound system for sonicating a target zone within the subject. The high-intensity focused ultrasound system comprises an ultrasound transducer for generating ultrasonic energy. The ultrasonic transducer comprises multiple ultrasound transducer elements. The phase and/or amplitude of each of the multiple ultrasound transducer elements are controllable. Execution of the instructions further causes the processor to calculate a set of transducer element phases and/or amplitude in accordance with the segmented medical image data and the speed of ultrasound in each of the at least two tissue types.

In another aspect the invention provides for a computer program product comprising machine executable instructions for execution by a processor controlling a medical apparatus. The computer program product may for instance be stored on a computer readable storage medium. The medical apparatus comprises an ultrasound transmitter and receiver system for acquiring ultrasound data. The ultrasound data is descriptive of the speed of ultrasound along the at least two paths in the subject or through the subject. The medical apparatus further comprises a medical imaging system for acquiring medical image data descriptive of the at least two paths in the subject.

Execution of the instructions causes the processor to acquire the medical image data using the medical imaging system. Execution of the instructions further causes the processor to acquire the ultrasound data using the ultrasound transmitter and receiver system. Execution of the instructions further causes the processor to segment the medical image data into at least two tissue types. Execution of the instructions further causes the processor to determine at least two distances in the subject for each of the at least two paths in the subject by the ultrasound. The at least two distances correspond to the distance traveled in the at least two tissue types by ultrasound generated by the ultrasound transmitter and receiver system. Execution of the instructions further causes the processor to calculate the speed of ultrasound in each of the at least two tissue types in accordance with the ultrasound data and with the at least two distances for each of the at least two paths.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
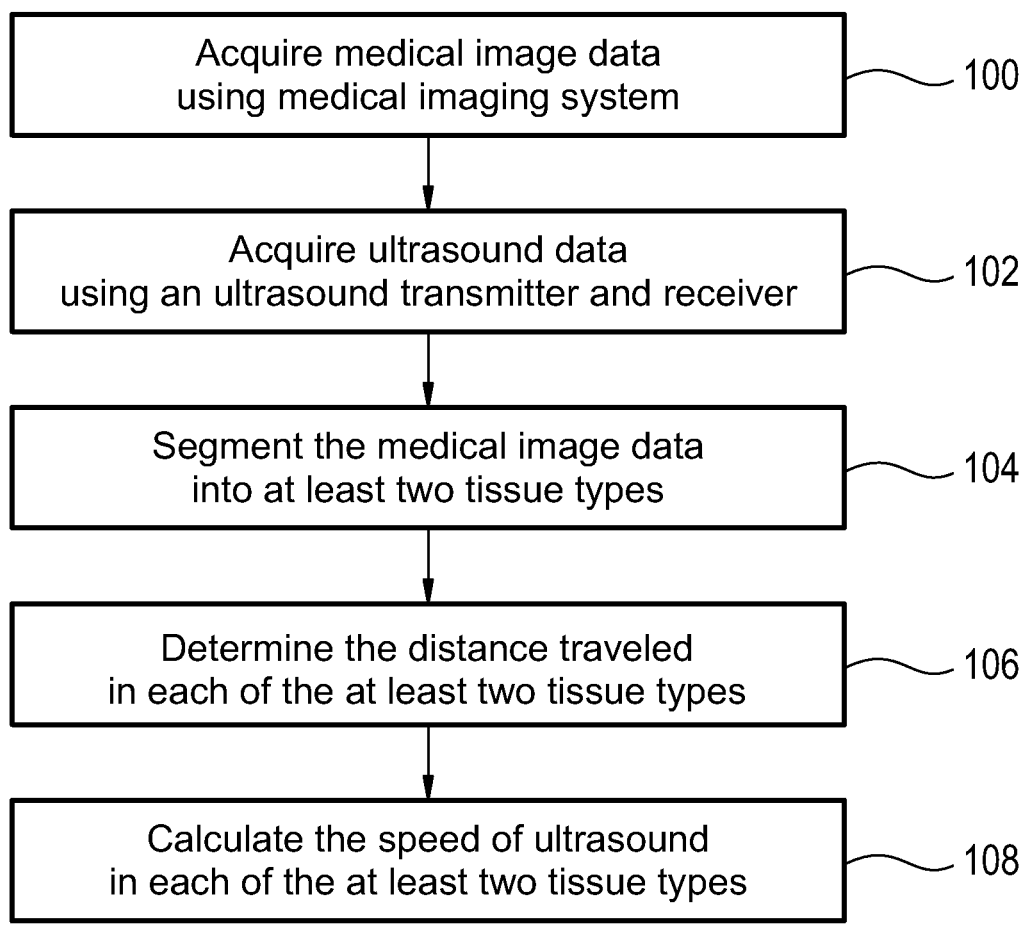
FIG. 1 shows a flow diagram which illustrates a method according to an embodiment of the invention.

FIG. 1 shows a flow diagram which illustrates a method according to an embodiment of the invention. In step 100 medical image data is acquired using a medical imaging system. Next in step 102 ultrasound data is acquired using an ultrasound transmitter and receiver. Steps 100 and 102 may be performed in any order or simultaneously with each other. Next in step 104 the medical image data is segmented into at least two tissue types. In step 106 the distance traveled in each of the at least two tissue types is determined. This may be accomplished by tracing the distance of at least two paths traveled by ultrasound generated by the ultrasound transmitter and receiver. Finally in step 108 the speed of ultrasound is calculated in each of the at least two tissue types. The calculation is done in accordance with the ultrasound data and the distances traveled in each of the at least two tissue types for at least two paths. The ultrasound data may contain information about the delay between the sending and receiving of the ultrasound by the transmitter and the receiver.

Figure 2:
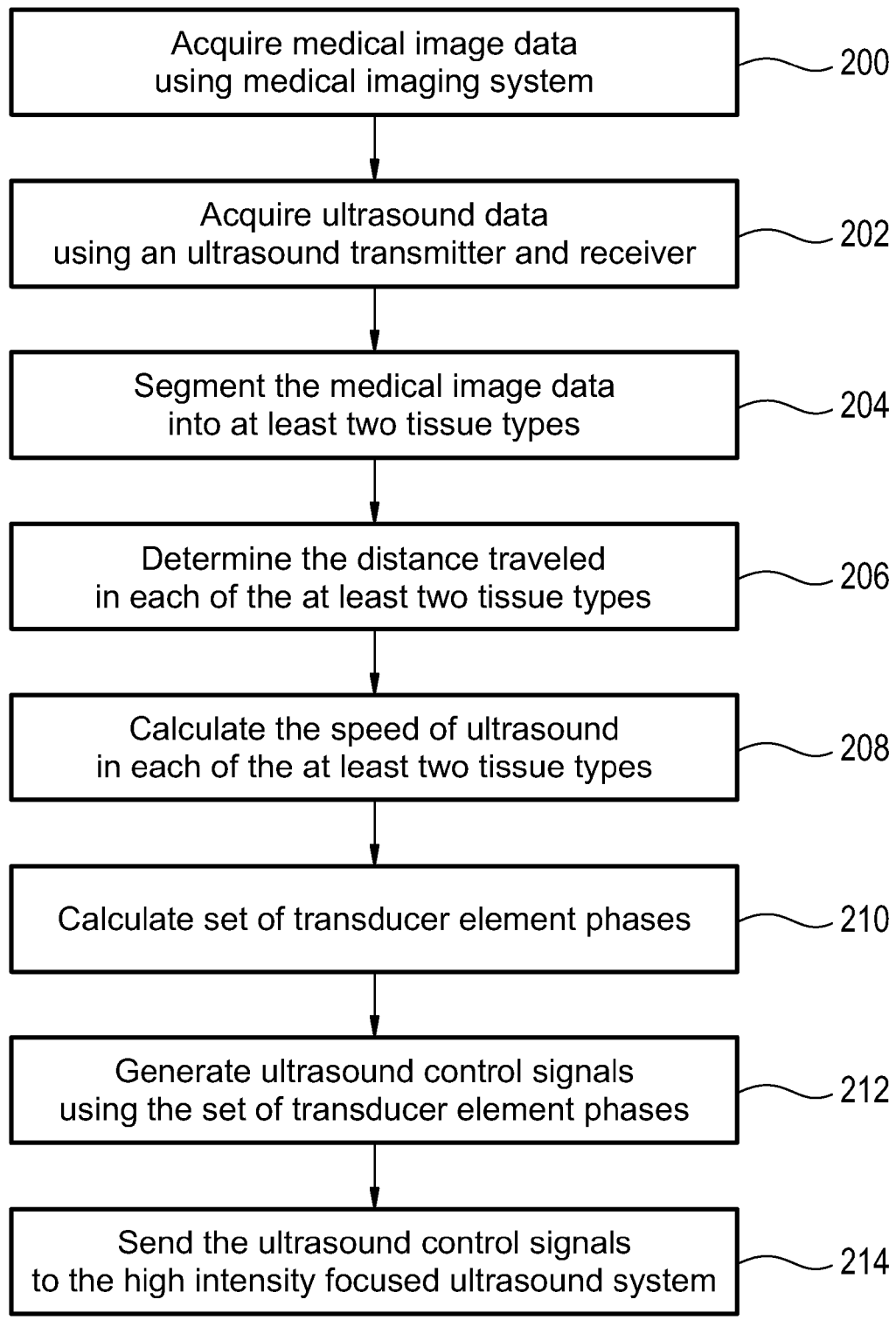
FIG. 2 shows a further embodiment of a method according to an embodiment of the invention.

FIG. 2 shows a flow diagram which shows a further embodiment of a method according to an embodiment of the invention. Steps 200-208 correspond to steps 100-108 of FIG. 1. In step 200 medical image data is acquired using the medical imaging system. In step 202 ultrasound data is acquired using an ultrasound transmitter and receiver. Data is acquired for at least two paths through the subject. In step 204 the medical image data is segmented into at least two tissue types. The number of paths through the subject should be at least as large as the number of tissue types. In step 206 the distance traveled in each of the at least two tissue types is determined. In step 208 the speed of ultrasound in each of the at least two tissue types is calculated. In step 210 a set of transducer element phases is calculated. In step 212 ultrasound control signals are generated using the set of transducer element phases. In step 214 the ultrasound control signals are sent to the high-intensity focused ultrasound system.

Figure 3:
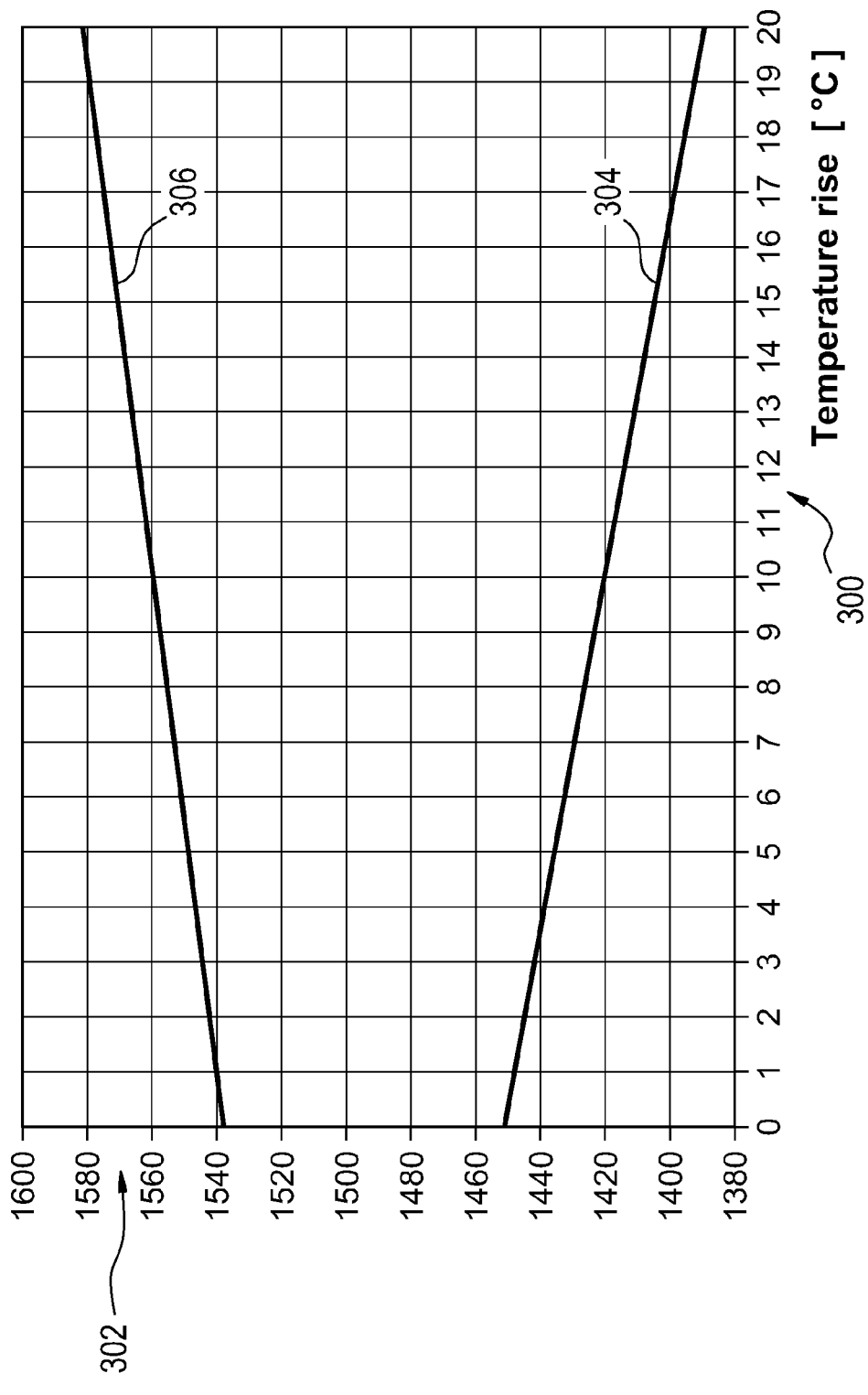
FIG. 3 shows a plot which illustrates the difference in ultrasound celerity for different tissue types in a human breast.

FIG. 3 shows a plot which illustrates the difference in ultrasound celerity for different tissue types in a human breast. On the x-axis is a temperature scale. It is measured in degrees Celsius and is relative to normal body core temperature. The y-axis 302 shows the celerity or ultrasound velocity in meters per second. The line labeled 304 is the velocity of ultrasound in breast fat. The line labeled 306 is the velocity of ultrasound in glandular tissue. It can be seen in this plot that the velocity of breast fat 304 and glandular tissue 306 is different. As the temperature increases this difference also becomes larger.

To illustrate the possibility to combine the ultrasound measurement means with of other image type than anatomical image and also the possibility to combine several imaging modalities together, we can consider the dependency of the celerity with the temperature.

For most of biologic tissues, the sound velocity increases with temperature with about 2.2 m s−1° C.−1 for a temperature range up to 50° C. In contrast, for lipids in interstitial tissue the velocity decreases with temperature with an estimated slope of −3.1 m/(s ° C.) for human breast fat.

In the literature it has reported that the celerity of breast glandular and breast fat is 1538 m/s and 1451 m/s, respectively, without any hyperthermia. Thus the FIG. 3 gives the celerity in function temperature rise assuming a constant slope of 2.2 m s−1° C.−1 and −3.1 m s−1° C.−1 for glandular and fatty tissue respectively based on literature. The difference of celerity in between fatty and glandular tissues increases by a factor 2 from 87 m/s to 174 m/s with a temperature rise of +16.4° C.

Since the phase correction designed to compensate the acoustic aberration in breast tissue is a function of the celerity, it is also a function of the temperature. The deference of celerity in between breast tissue increases by a factor 2 during typical hyperthermia of 16.4° C., thus it appears that quantification of temperature distribution for the adjustment of the temperature is as much essential as the initial quantification of the celerity without hyperthermia.

Embodiments of a method according to the invention may comprise measuring the temperature distribution within breast tissue to make celerity quantification adjustments. The spatial temperature distribution can be measured also by MRI using one or several temperature mapping based on proton resonance frequency shift (especially for glandular tissue) and/or thermal map based on T1, T2 or T2-star relaxation change (especially for fatty tissue).

For a patient-specific adaptation of the temperature dependency of the celerity for each tissue type, it might be possible to perform ultrasound measurements simultaneously to the therapy procedure, by switching rapidly in between sonication and ultrasound measurement, or doing both simultaneously if no interference occurred. The thermal maps and the ultrasound measurements acquired on the fly can be used to estimate ultrasound tissues characteristics in real time for each tissue type. For example the previous equations can be reused with a subdivision of each tissue layer in smaller regions with similar temperature. As the result, the celerity and the attenuation in each small region is obtained for each temperature change occurring. However, the large number of small regions will require a large number of ultrasound emitter and receivers. To keep this system simple, the alternative way to solve this equation could be an iterative search of the appropriate temperature dependency of the celerity per tissue type which matches the best to ultrasound measurement.

Figure 4:
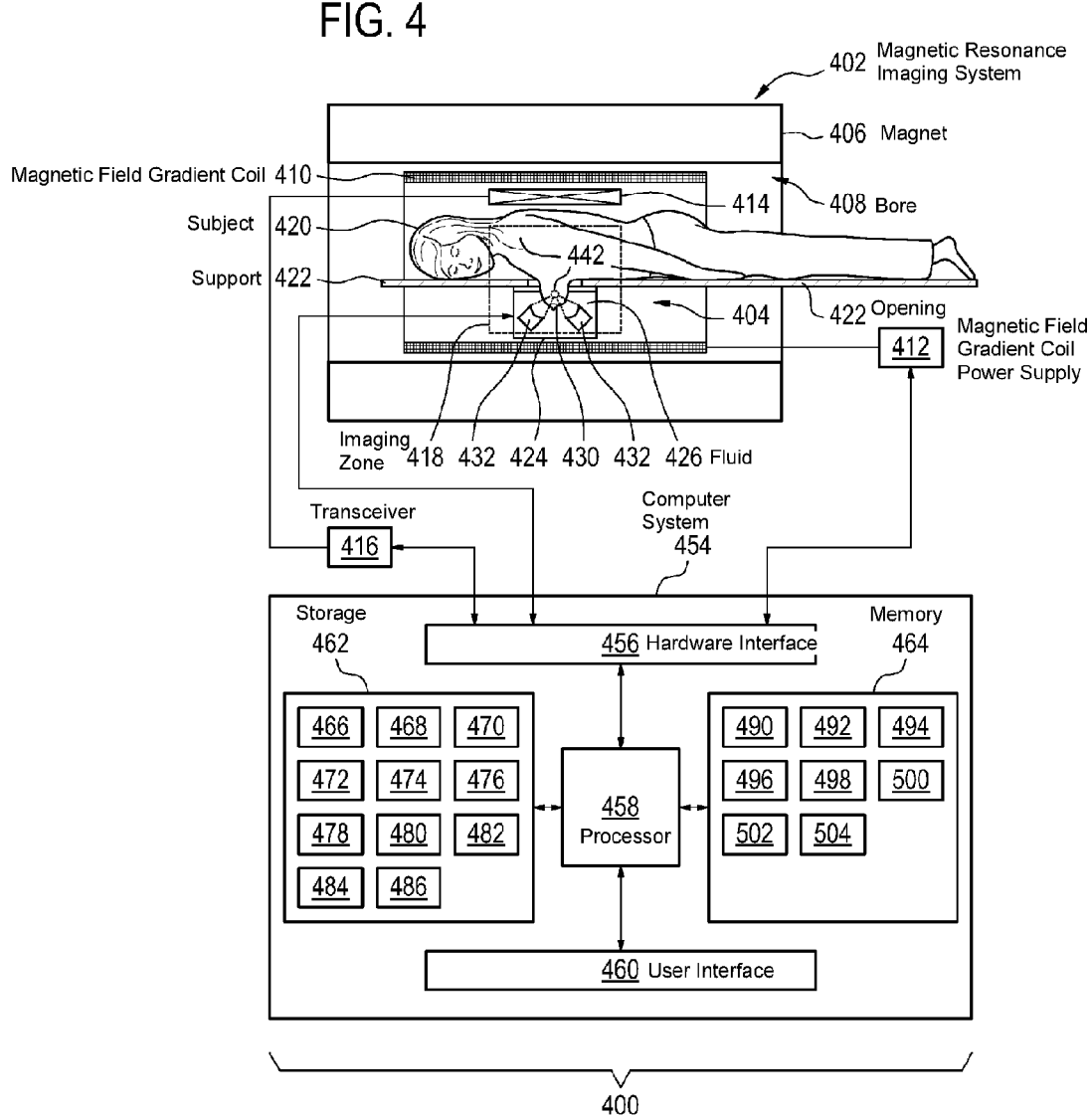
FIG. 4 illustrates a medical apparatus according to an embodiment of the invention.

FIG. 4 shows a diagram which illustrates a medical apparatus 400 according to an embodiment of the invention. In this embodiment the medical apparatus 400 comprises a magnetic resonance imaging system 402 and a high-intensity focused ultrasound system 404.

Figure 5:
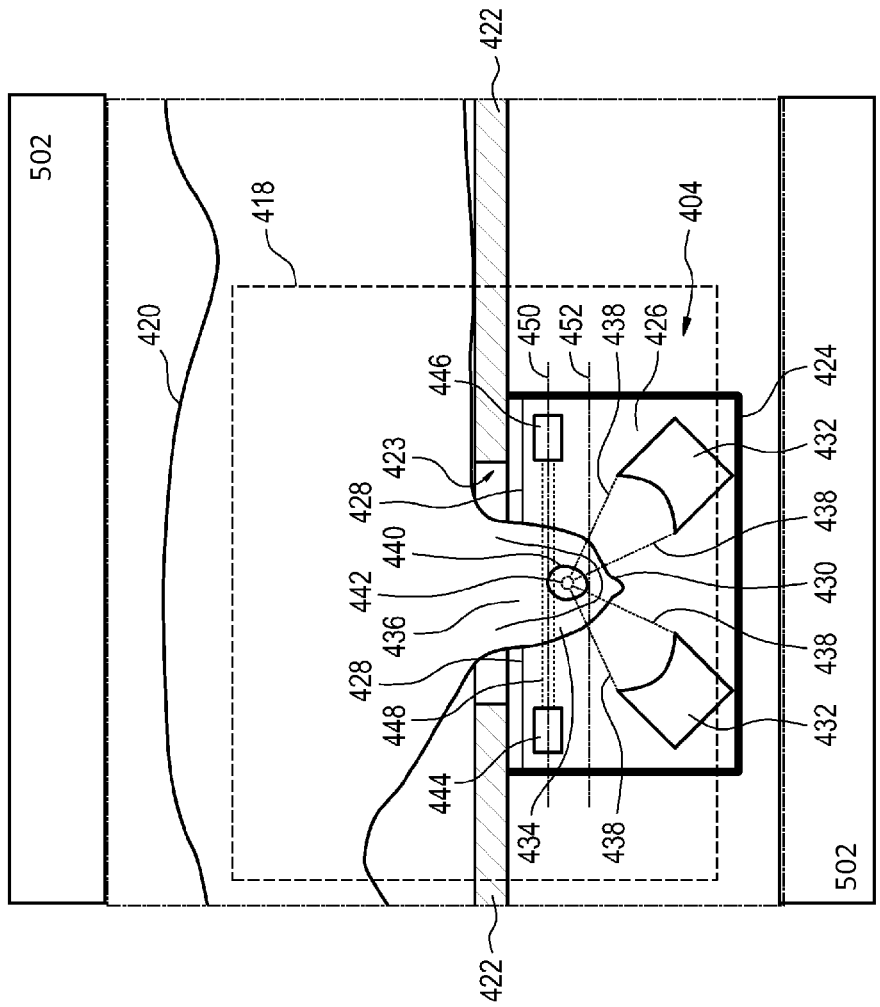
FIG. 5 shows a more detailed illustration of the high-intensity focused ultrasound system of the embodiment of FIG. 4.

FIG. 5 shows a more detailed drawing of the high-intensity focused ultrasound system 404. In this embodiment an imaging system 502 is used. The magnetic resonance imaging system 402 of FIG. 4 is intended to be exemplary. In other embodiments other medical imaging systems could be used also. For instance the magnetic resonance imaging system

402 of FIG. 4, a computer tomography system or a diagnostic ultrasound system may be used as the imaging system 502. FIG. 4 and FIG. 5 are described together.

The magnetic resonance imaging system 402 comprises a magnet 406. The magnet 406 is a cylindrical superconducting type magnet and has a bore 408 through it. The magnet 406 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 408 of the cylindrical magnet there is an imaging zone 418 where the magnetic field is strong and uniform enough to perform magnetic resonance imaging.

Within the bore of the magnet there is also a magnetic field gradient coil 410 which is used for acquisition of magnetic resonance data and to spatially encode magnetic spins within the imaging zone 418 of the magnet 406. The magnetic field gradient coil 410 is connected to a magnetic field gradient coil power supply 412. The magnetic field gradient coil 410 is intended to be representative. Typically magnetic field gradient coils 410 contain three separate sets of coils for spatially encoding in three orthogonal spatial directions. A magnetic field gradient power supply 412 supplies current to the magnetic field gradient coils. The current supplied to the magnetic gradient field coils 410 is controlled as a function of time and may be ramped or pulsed.

Adjacent to the imaging zone 418 is a radio-frequency coil 414 for manipulating the orientations of magnetic spins within the imaging zone 418 and for receiving radio transmissions from spins also within the imaging zone 418. The radio frequency antenna may contain multiple coil elements. The radio-frequency coil may also be referred to as a channel, an antenna, or a radio-frequency antenna. The radio-frequency coil is connected to a radio frequency transceiver 416. The radio-frequency coil 414 and radio-frequency transceiver 416 may be replaced by separate transmit and receive coils and a separate transmitter and receiver. It is understood that the radio-frequency coil 414 and the radio frequency transceiver 416 are representative. The radio frequency antenna is intended to also represent a dedicated transmit antenna and a dedicated receive antenna. Likewise the transceiver 416 may also represent a separate transmitter and receivers.

There is a subject 420 reposing on a subject support 422 within the bore 408 of the magnet 406. A part of the subject 420 is within the imaging zone 418. The high-intensity focused ultrasound system 404 has a tank 424. The tank 424 is filled with an ultrasound conducting fluid 426. The top of the fluid or the fluid level is indicated by the markers 428. A portion 430 of the subject 420 goes through an opening 423 in the subject support 422 and the tank 424. The portion 430 extends and is partially surrounded by the ultrasound conducting fluid 426. In this example two ultrasonic transducer elements 432 are shown as being within the fluid 426. The portion 430 of the subject 420 is a breast. There are two regions of tissue; there is a fat tissue 434 region and a glandular tissue 436 region. The dashed lines 438 trace the path of ultrasound 438 from the ultrasonic transducer elements 432 through the fluid 426, through the fat tissue 434, and through the glandular tissue 436 to a sonication volume 442 which is located within a target volume 440.

Above the ultrasonic transducer elements is an ultrasonic transmitter 444 and an ultrasonic receiver 446. There is an ultrasound beam 448 traveling from the ultrasound transmitter 444 to the ultrasound receiver 446. There is a first plane 450 and a second plane 452 which are indicated by dashed lines. The ultrasound transmitter 444 and the ultrasound receiver 446 are primarily located within the first plane 450. The ultrasound travels primarily through the first plane. There is a second plane 452. The second plane 452 is located below the first plane 450. The ultrasonic transducer elements 432 are located below the first plane 452 but the sonication volume 442 is located above the second plane 452. This embodiment is advantageous because it allows a direct measurement of the ultrasound velocity within the breast tissue in close proximity to the sonication volume 442. In fact in some embodiments the sonication volume 442 is also located primarily in the first plane 450. The plane 450 is of course a two-dimensional space. The ultrasound beam 448 and the sonication volume 442 are three-dimensional volumes. If a plane cuts through a portion of the volume then the volume is, as used in this document, primarily within that plane.

The high-intensity focused ultrasound system 404; the magnetic field gradient coil power supply 412 and the transceiver 416 are shown as being connected to a hardware interface 456 of a computer system 454. The hardware interface 456 is connected to a processor 458. The processor 458 is further connected to a user interface 460, computer storage 462, and computer memory 464.

The computer storage 462 is shown as containing magnetic resonance data 466 acquired by the magnetic resonance imaging system 402. There is magnetic resonance image data 468 which has been reconstructed from the magnetic resonance data 466. Magnetic resonance image data 468 is an example of medical image data. Also within the computer storage 462 is stored an image segmentation 470 of the magnetic resonance image data 468. The image segmentation 470 contains information which is descriptive of the location of the at least two tissue types 434, 436. Within the computer storage there is a thermal map 472. The thermal map is reconstructed from the magnetic resonance data 466. The magnetic resonance data comprises magnetic resonance thermometry data. The computer storage is also shown as containing distance data 474. The distance data is descriptive of the distance that the ultrasound beam 448 traveled through the first and second 434, 436 tissue types. The first tissue type is the fat tissue 434 and the second tissue type is the glandular tissue 436. The computer storage is shown as containing ultrasound data 476. The ultrasound data is data acquired by the ultrasound receiver 446.

The computer storage is shown as containing pulse delay data 478 and amplitude data 480 extracted from the ultrasound data 476. The pulse delay data 478 is descriptive of the delay in the ultrasound beam 448 traveling from the transmitter 444 to the receiver 446. The amplitude delay data 480 is descriptive of the change in amplitude from the transmitter 444 to the receiver 446. The computer storage is further shown as containing ultrasound control signals 484. The ultrasound control signals contain instructions for operating the high-intensity focused ultrasound system 404. The computer storage is shown as containing ultrasound velocities 486 which were calculated using the pulse delay data 478 and the distance data 474. The distance data 474 and the amplitude delay data 480 may be used for calculating ultrasound attenuation in the two tissue types 434, 436.

Computer memory 464 is shown as containing a control module 490. The control module 490 contains computer executable code for controlling the operation and functioning of the medical apparatus 400. The computer memory 464 is further shown as containing a pulse sequence 492 which contains the operations performed by the magnetic resonance imaging system 402 to acquire the magnetic resonance data 466. There is a magnetic resonance imaging system control module 494 which uses the pulse sequence 492 to control the magnetic resonance imaging system 402. The computer memory 464 is further shown as containing an image module 496. The image module 496 contains computer executable code for reconstructing the magnetic resonance data 466 into the magnetic resonance image data 468 and/or for performing and generating the image segmentation 470 from the magnetic resonance image data 468. The image module 496 may also contain computer executable code for generating the thermal map 472 from the magnetic resonance data 466.

The computer memory 464 is further shown as containing a high-intensity focused ultrasound control module 498. The high-intensity focused ultrasound control module 498 contains computer executable code for controlling the operation and function of the high-intensity focused ultrasound system 404. The high-intensity focused ultrasound control module 498 is adapted for generating the ultrasound control signals 484. The computer memory 464 is shown as further containing an image analysis module 500. The image analysis module is able to calculate the distance data 474 using the image segmentation 470 and the magnetic resonance image data 468.

The computer memory 464 is further shown as containing a velocity calculation module 502 and an attenuation calculation module 504. The velocity calculation module contains computer executable code adapted for calculating the ultrasound velocities 486 from the distance data 474 and the pulse delay data 478. The attenuation calculation module 504 contains computer executable code for calculating ultrasound attenuation using the amplitude data 480 and the distance data 474.

Figure 6:
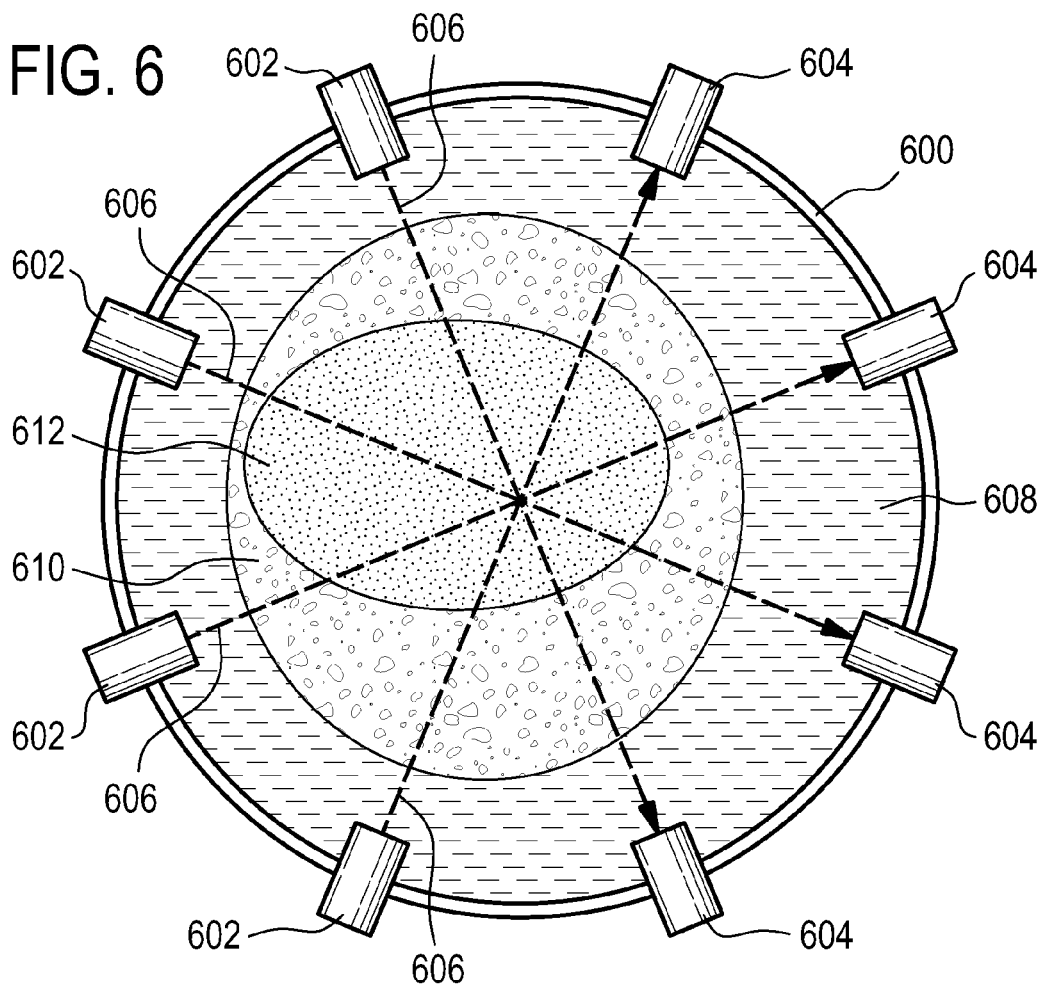
FIG. 6 shows an example of an ultrasound transmitter and receiver system according to an embodiment of the invention.

FIG. 6 shows an example of an ultrasound transmitter and receiver system 600 according to an embodiment of the invention. In this Fig. four transmitters 602 are shown. Across from each transmitter 602 is a receiver 604. The dashed lines indicated with 606 trace a path from a transmitter 602 to a receiver 604. The paths 606 travel through ultrasonic conducting fluid 608, a first tissue type 610 and a second tissue type 612. To determine the velocity in the first and second tissue types 610, 612 a medical imaging system could acquire medical image data in the same plane in which the paths 606 lie. For each path the distance traveled in the ultrasonic conducting fluid 606, the first tissue type 610 and the second tissue type 612 can be calculated. By determining the delay between the transmissions from a transmitter 602 to the receiver 604 the velocity in the ultrasonic conducting fluid and each of the tissue types 610, 612 can be calculated.

Prior to any MR-HIFU treatment, patient undergoes various types of medical exams to establish diagnostic. This screening stage is essential to predict the success of the HIFU treatment relatively to other treatment types. The use of combined means to characterize ultrasound tissues properties with the screening imaging modalities (other than ultrasound celerity measurement) can be used to improve the treatment option.

For HIFU treatment of breast cancer the knowledge of celerity and shape of tissues is essential, since the resulting phase aberration can be corrected only in limited range of values. Thus a simulation of the acoustic field based on tissue model obtained with the method previously described can provide answers to the possibility to treat the patient by HIFU.

For such screening process, the ultrasound measurement means can be integrated inside a system combining one or several imaging modalities (other than ultrasound celerity measurement) independently of the HIFU system, in order to determine ultrasound celerity and attenuation of each tissues type with the same method as the one previously described.

For example, the ring structure described in FIG. 6 can be inserted into a MRI Mammography track table usually used to detected breast cancer. A MRI mammography track table is equivalent with the subject support 442 shown in FIGS. 4 and 5. In this case, ultrasound emitters and receivers can be placed to propagate the acoustic wave in between MR coil receiver loops.

Once the ultrasound celerity and attenuation of each tissues type are quantified during the patient screening step and the patient is eligible for HIFU treatment, the resulting characterizations of tissues can be reused for treatment procedure. Since ultrasound celerity and attenuation of each tissue are most probably the same on screening day and treatment day, only a registration of segmented tissue layers or a new segmentation of tissue layers is necessary to process the phase and intensity correction to apply to refocus the beam. Of course, if necessary, the ultrasound celerity and attenuation measurement can re-acquired on treatment day if it is wanted to ensure the reliability of those measurement. However if those measurements are time consuming and were already acquired during screening step, new quantifications of ultrasound celerity and attenuation could be avoided on treatment day in order to reduce the total treatment duration.

A Magnetic Resonance-High intensity focused ultrasound (MR-HIFU) platform can include ultrasound emitters/receivers system in charge to quantify celerity of tissue volume segmented by MRI. In the example shown in FIG. 6, this system is composed of 4 emitters placed in front of 4 receivers attached to a rigid ring in order to characterize breast tissues along 4 directions.

The emission and reception of ultrasonic pulses provide the ultrasound travelling times $T_i$ and pressure amplitudes $P_i$ along each direction i. Similarly, quantification of $T^{Ref}_i$ and $P^{Ref}_i$ can be also be done in a previous system calibration step, using water only or oil only, according to coupling medium between the breast and transducers. The measurement duration along one line is very fast since ultrasound travelling time over a distance of 15 cm is about 0.1 ms. Thus measurements can be repeated for averaging purpose without inducing significant delay of the therapy procedure duration. Such averaging improves the accuracy of the measurement of the delay and the pressure amplitude.

Segmentation algorithm of MR images provides delineation of fat tissue F, glandular tissues G and water W. Intersection of lines running from emitters to receivers across each medium surface provides quantification of lengths $L^W_i$, $L^F_i$ and $L^G_i$. However the quantification of lengths $L^W_i$ is not mandatory.

Travelling times are linked to each other by the celerity $C^F$, $C^G$, $C^W$ and the attenuation $A^F$, $A^G$, $A^W$ of the water, fat and glandular medium according to those linear equations:

$$\begin{bmatrix} T_1 \\ T_2 \\ T_3 \\ T_4 \end{bmatrix} = \begin{bmatrix} L_1^W & L_1^F & L_1^G \\ L_2^W & L_2^F & L_1^G \\ L_3^W & L_3^F & L_1^G \\ L_4^W & L_4^F & L_1^G \end{bmatrix} \times \begin{bmatrix} 1/C^W \\ 1/C^F \\ 1/C^G \end{bmatrix} \text{ and}$$

$$\begin{bmatrix} T_1^{Ref} \\ T_2^{Ref} \\ T_3^{Ref} \\ T_{14}^{Ref} \end{bmatrix} = \begin{bmatrix} L_1^W & L_1^F & L_1^G \\ L_2^W & L_2^F & L_1^G \\ L_3^W & L_3^F & L_1^G \\ L_4^W & L_4^F & L_1^G \end{bmatrix} \times \begin{bmatrix} 1/C^W \\ 1/C^W \\ 1/C^W \end{bmatrix}$$

The subtraction of both equations cancels lengths $L_i^W$ which makes quantification of breast tissues celerity more accurate. The measurement of length $L_i^W$ by MRI are inaccurate due to the image distortion at proximity of a transducer related to the sharp change of magnetic susceptibility field. The difference of propagation time between $T_i^{Ref}$ and $T_i$ corresponds to a comparison of two similar wave forms which can be very precisely evaluated by a cross correlation.

$$\begin{bmatrix} T_1 - T_1^{Ref} \\ T_2 - T_2^{Ref} \\ T_3 - T_3^{Ref} \\ T_4 - T_4^{Ref} \end{bmatrix} = \begin{bmatrix} L_1^F & L_1^G \\ L_2^F & L_1^G \\ L_3^F & L_1^G \\ L_4^F & L_1^G \end{bmatrix} \times \begin{bmatrix} 1/C^F - 1/C^W \\ 1/C^G - 1/C^W \end{bmatrix}$$

It results that celerity $C^F$ are $C^G$ are obtained by inversion of the previous equation:

$$\begin{bmatrix} 1/C^F \\ 1/C^G \end{bmatrix} = \begin{bmatrix} 1/C^W \\ 1/C^W \end{bmatrix} + \begin{bmatrix} \sum_i L_i^F L_i^F & \sum_i L_i^F L_i^G \\ \sum_i L_i^F L_i^G & \sum_i L_i^G L_i^G \end{bmatrix}^{-1} \times \begin{bmatrix} \sum_i L_i^F (T_i - T_i^{Ref}) \\ \sum_i L_i^G (T_i - T_i^{Ref}) \end{bmatrix}$$

Similarly pressure amplitudes are linked to each other by the attenuation $\alpha^F$, $\alpha^G$, $\alpha^W$ of the water, fat and glandular medium and emitted pressure amplitude $P_0$ according to those linear equations:

$$\begin{bmatrix} \ln(P_1/P_0) \\ \ln(P_2/P_0) \\ \ln(P_3/P_0) \\ \ln(P_4/P_0) \end{bmatrix} = \begin{bmatrix} L_1^W & L_1^F & L_1^G \\ L_2^W & L_2^F & L_1^G \\ L_3^W & L_3^F & L_1^G \\ L_4^W & L_4^F & L_1^G \end{bmatrix} \times \begin{bmatrix} \alpha^W \\ \alpha^F \\ \alpha^G \end{bmatrix} \text{ and}$$

$$\begin{bmatrix} \ln(P_1^{Ref}/P_0) \\ \ln(P_2^{Ref}/P_0) \\ \ln(P_3^{Ref}/P_0) \\ \ln(P_4^{Ref}/P_0) \end{bmatrix} = \begin{bmatrix} L_1^W & L_1^F & L_1^G \\ L_2^W & L_2^F & L_1^G \\ L_3^W & L_3^F & L_1^G \\ L_4^W & L_4^F & L_1^G \end{bmatrix} \times \begin{bmatrix} \alpha^W \\ \alpha^W \\ \alpha^W \end{bmatrix}$$

The subtraction of both equations cancels lengths $L_i^W$ and pressure amplitude $P_0$ which makes quantification of tissue attenuation more accurate.

$$\begin{bmatrix} \ln(P_1/P_1^{Ref}) \\ \ln(P_2/P_2^{Ref}) \\ \ln(P_3/P_3^{Ref}) \\ \ln(P_4/P_4^{Ref}) \end{bmatrix} = \begin{bmatrix} L_1^F & L_1^G \\ L_2^F & L_1^G \\ L_3^F & L_1^G \\ L_4^F & L_1^G \end{bmatrix} \times \begin{bmatrix} \alpha^F - \alpha^W \\ \alpha^G - \alpha^W \end{bmatrix}$$

It results that celerity $\alpha^F$ and $\alpha^G$ are obtained by inversion of the previous equation:

$$\begin{bmatrix} \alpha^F \\ \alpha^G \end{bmatrix} = \begin{bmatrix} \alpha^W \\ \alpha^W \end{bmatrix} + \begin{bmatrix} \sum_i L_i^F L_i^F & \sum_i L_i^F L_i^G \\ \sum_i L_i^F L_i^G & \sum_i L_i^G L_i^G \end{bmatrix}^{-1} \times \begin{bmatrix} \sum_i L_i^F \ln(P_i/P_i^{Ref}) \\ \sum_i L_i^G \ln(P_i/P_i^{Ref}) \end{bmatrix}$$

This method can be generalized to characterize more than 2 tissue types until the number of tissue types is lower or equal than the number of measurements direction. However a better measurement accuracy of tissues characteristics is obtained when the number of direction is larger than the number of tissue types such as this example with 2 tissue type and 4 directions.

Figure 7:
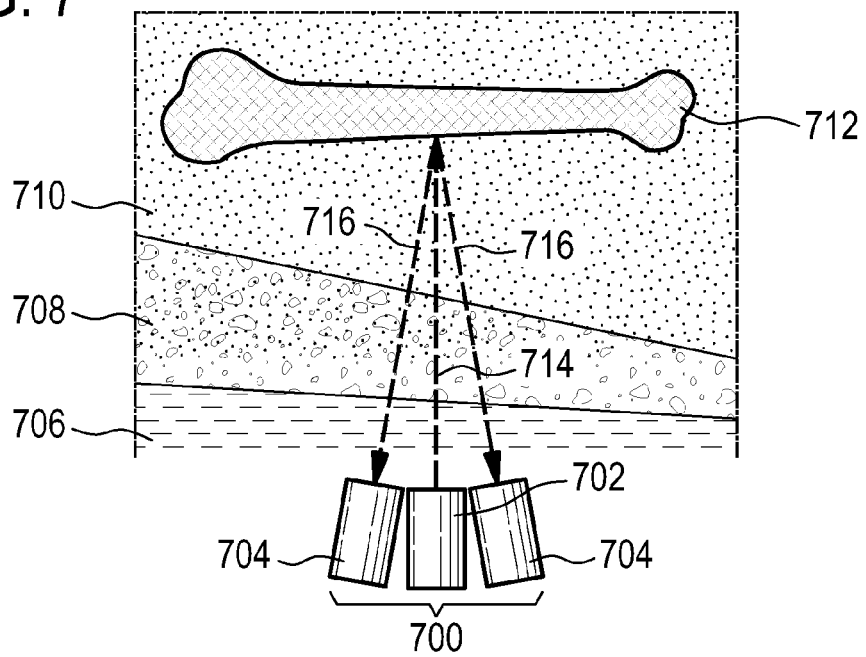
FIG. 7 shows an ultrasound transmitter and receiver system according to a further embodiment of the invention.

FIG. 7 shows an ultrasound transmitter and receiver system 700 according to an embodiment of the invention. In this example there is a single transmitter 702 and multiple receivers 704, a region of ultrasonic conducting fluid 706, a first tissue type 708, a second tissue type 720, and boney tissue 712. Ultrasound travels from the transmitter 702 through the ultrasonic conducting fluid, the first tissue type 708, the second tissue type 710 along path 714. The ultrasound is then reflected by the bone 712. The dashed line 716 shows the path of the ultrasound back to the receivers 704. Medical image data acquired in the plane of the path 714 and 716 may be used to calculate the distance traveled in the ultrasonic conducting fluid, the first tissue type 708 and the second tissue type 710. This may be used in conjunction with the delay between the ultrasound being transmitted 702 and being received by the different receiver 704 to calculate the velocity of ultrasound in the tissue types.

Alternative method could be considered using reflection of ultrasound wave over the bone to characterize subcutaneous fat and muscle in other body regions. Bone structures are frequently encountered during treatment of bone metastasis as well as liver and kidney cancer.

Figure 8:
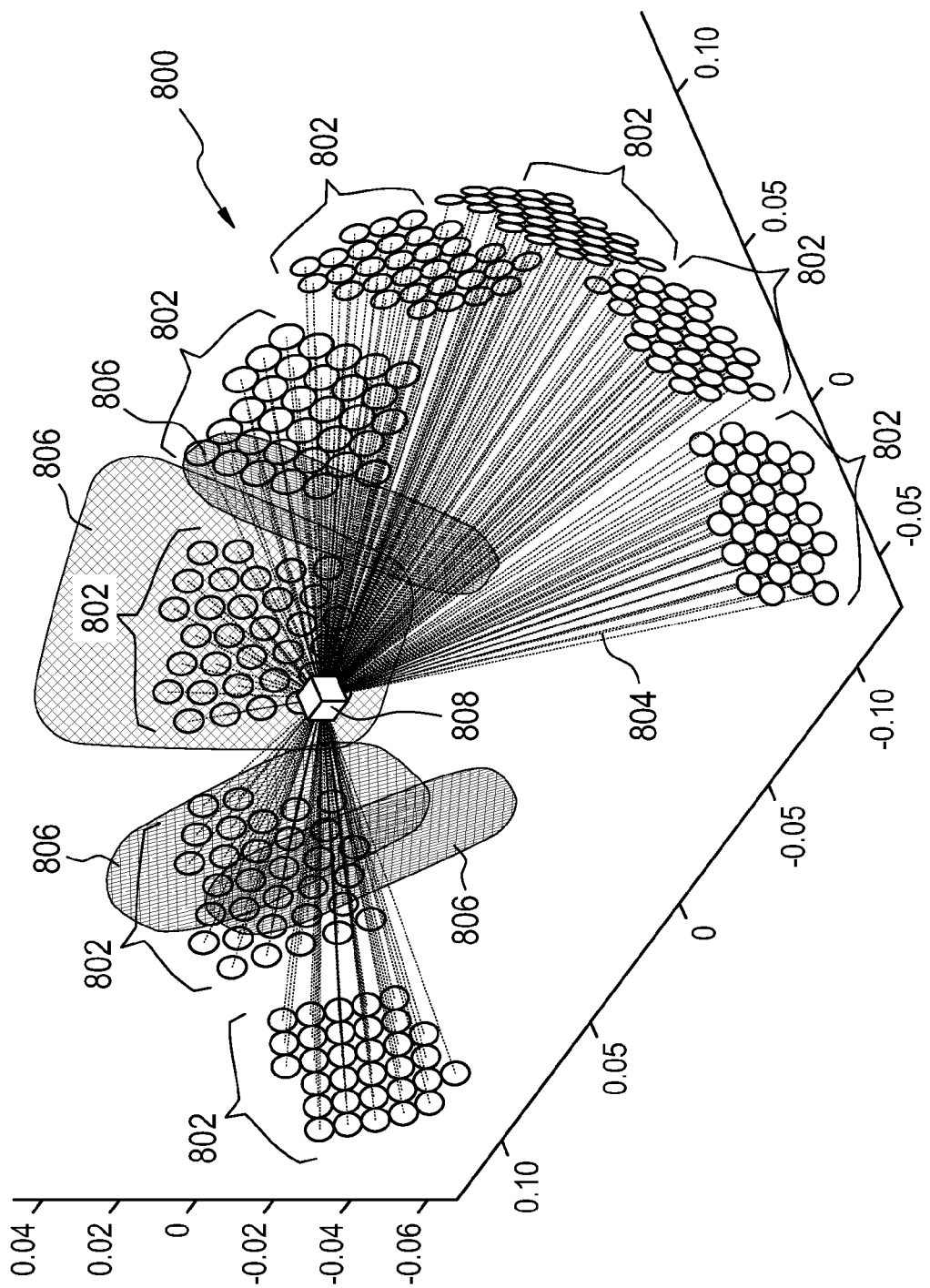
FIG. 8 shows an isometric view of an arrangement of ultrasonic transducer elements according to an embodiment of the invention.
Figure 9:
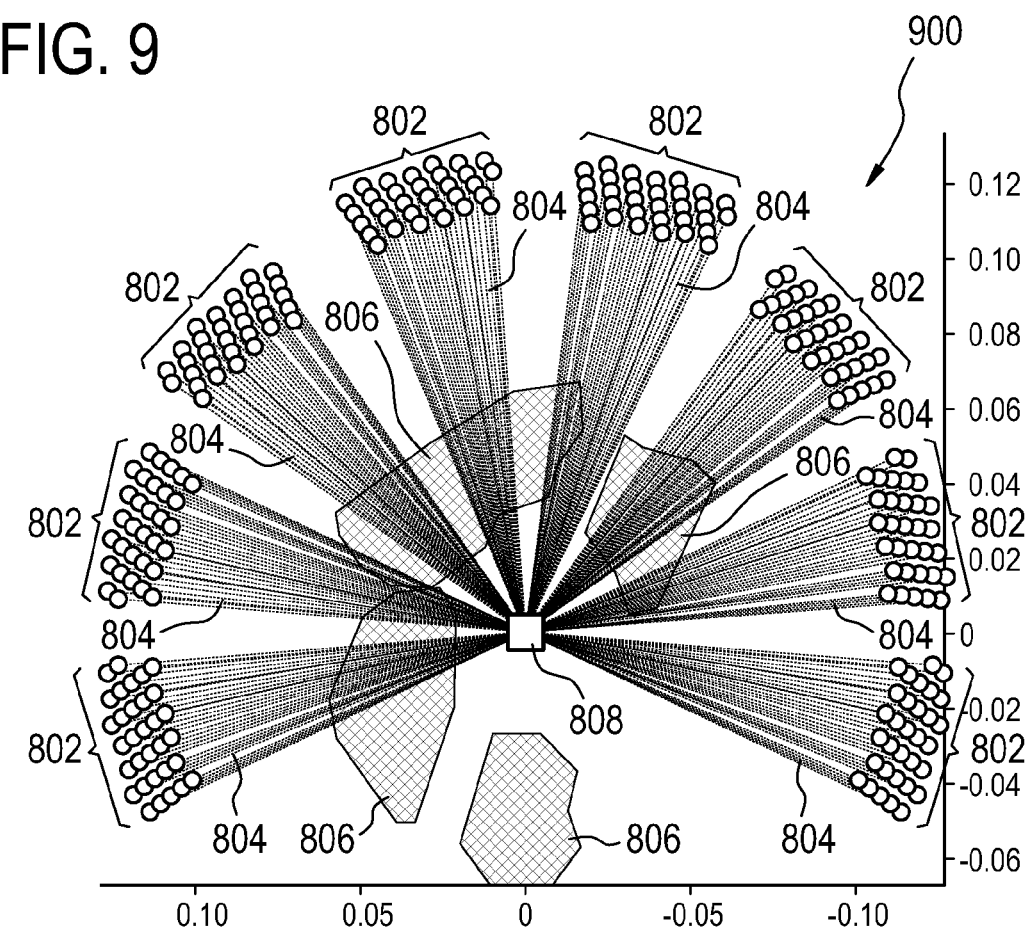
FIG. 9 shows a top view of an arrangement of ultrasonic transducer elements for the embodiment of FIG. 8.
Figure 10:
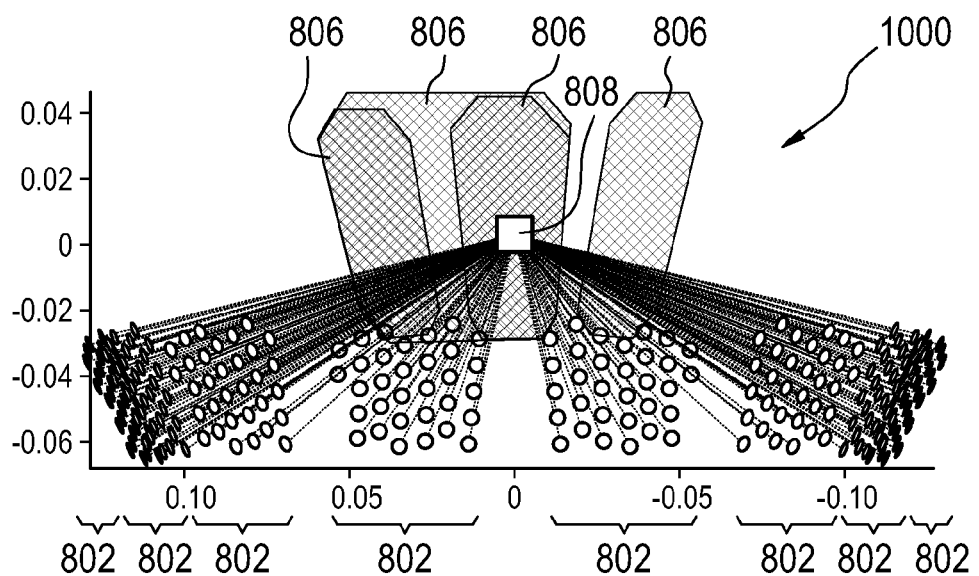
FIG. 10 shows a side view of an arrangement of ultrasonic transducer elements for the embodiment of FIG. 8.

FIGS. 8, 9 and 10 show a iso-metric view 800, a top view 900, and a side view 1000 of an arrangement of ultrasonic transducer elements 802. Each of the little circles is a single ultrasonic transducer element. The dashed lines 804 show the path of ultrasound to a sonication volume 808. For reference the shapes 806 show the same tissue structure in the three different views 800, 900, and 1000.

FIGS. 11-15 show different configurations of the ultrasound transmitter and receiver system in relation to the ultrasound transducer of a high-intensity focused ultrasound system.

Figure 11:
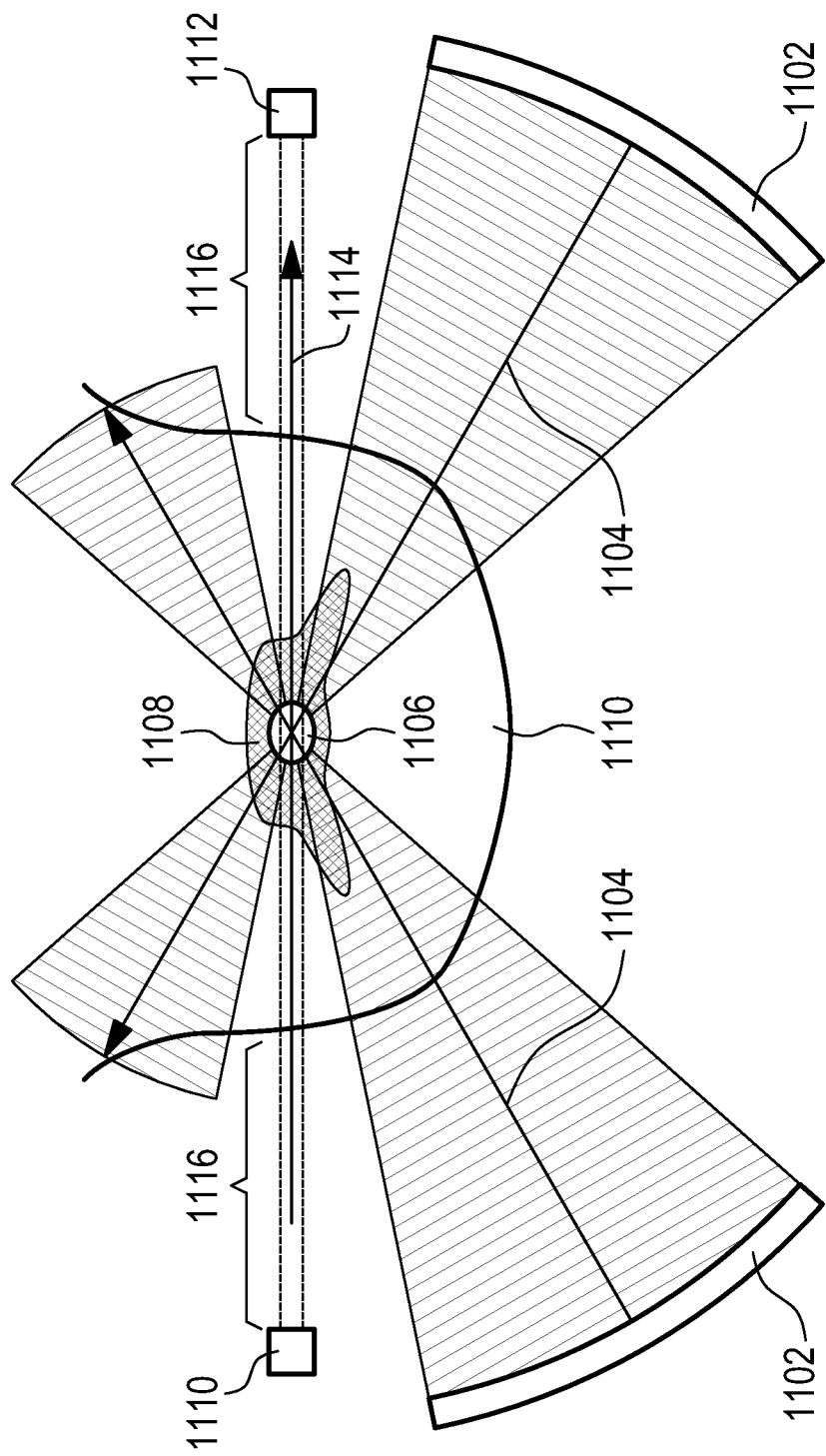
FIG. 11 illustrates the relative position of an ultrasound transmitter and receiver system in relation to a ultrasound transducer of a high-intensity focused ultrasound system according to an embodiment of the invention.

In FIG. 11 the region 1100 represents the subject. There are two ultrasound transducer elements shown. The arrows marked 1104 and the surrounding cone-like area shows the path of the therapeutic ultrasound 1104 where it is focused into a sonication volume 1106 within the subject 1100. There is a heated region 1108 surrounding the sonication volume 1106. The ultrasound transducer elements 1102 are focused upwards in this embodiment. In a plane located above the ultrasound transducer elements 1102 there is a transmitter 1110 and receiver 1112 for transmitting ultrasound pulses along a path 1114 through the subject. In this embodiment there is a space between the subject 1100 and the transmitter 110 and there is also a space 1116 between the subject 1100 and the receiver 1112.

Figure 12:
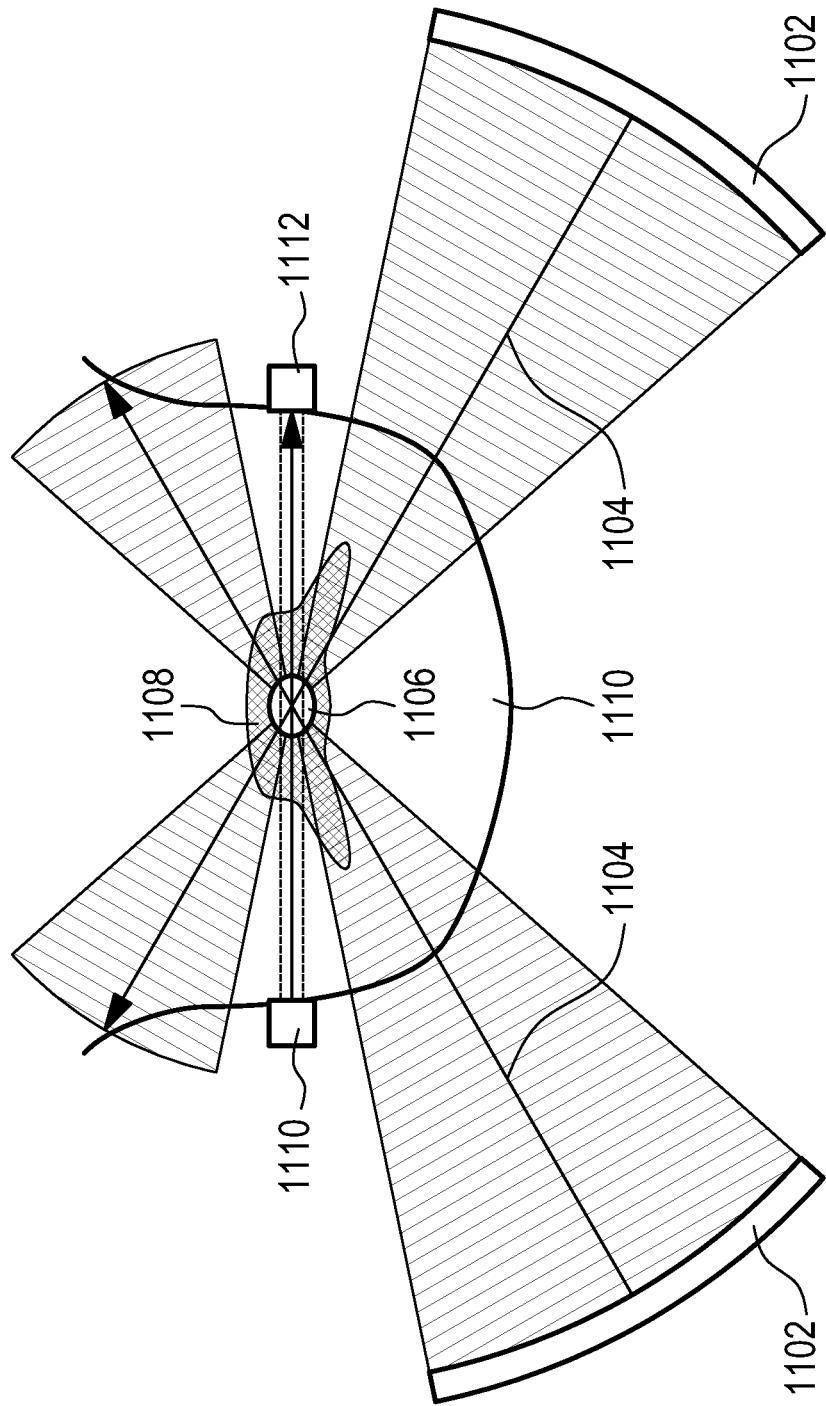
FIG. 12 illustrates the relative position of an ultrasound transmitter and receiver system in relation to a ultrasound transducer of a high-intensity focused ultrasound system according to a further embodiment of the invention

FIG. 12 shows a very similar embodiment except in this embodiment there is no space. The transmitter 1110 is directly in contact with the subject 1100. The receiver 1112 is also directly in contact with the subject 1100. In the previous embodiment of FIG. 11 the space 1116 may for instance be filled with a gel pad or other similar ultrasound conducting medium.

Figure 13:
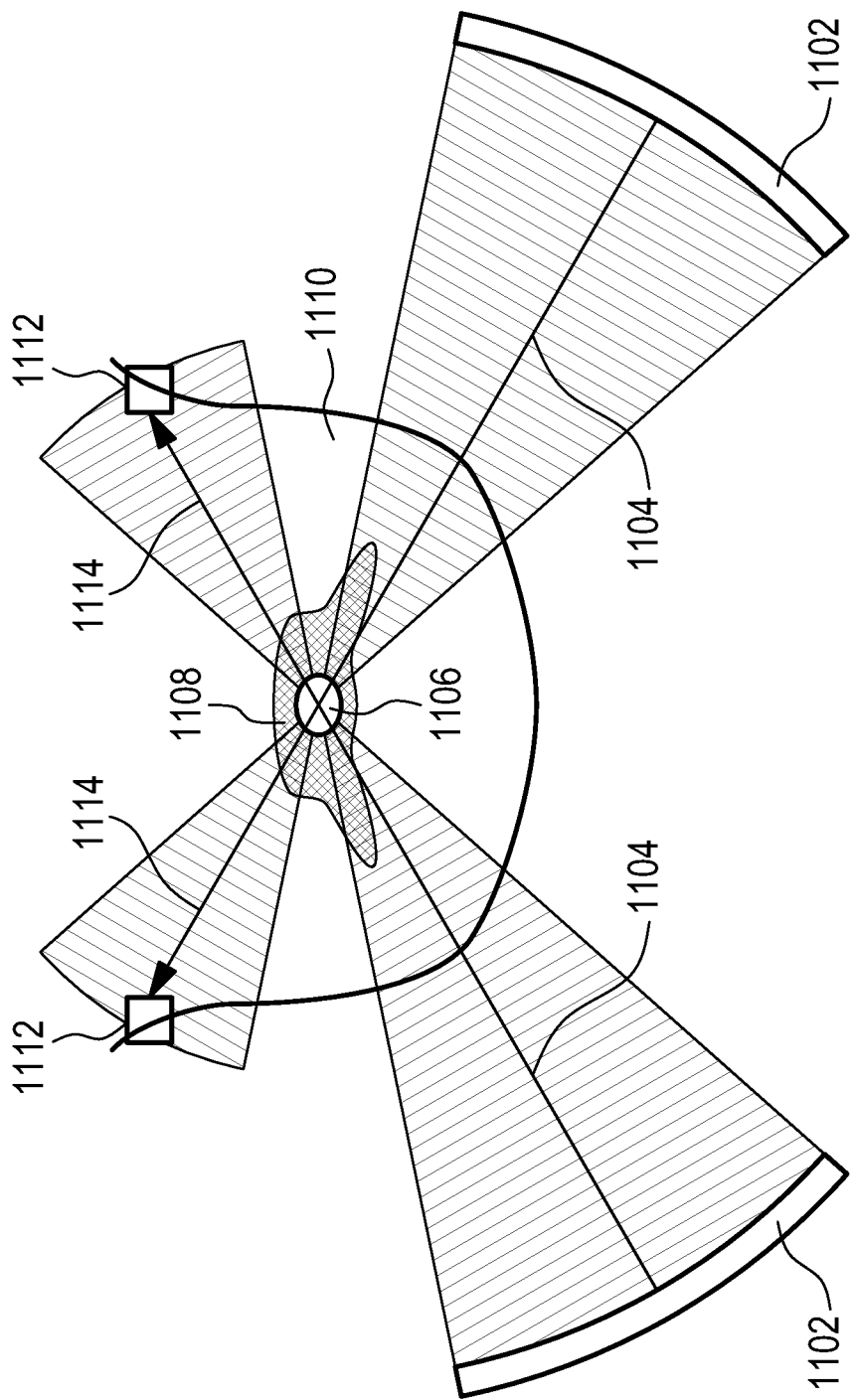
FIG. 13 illustrates the relative position of an ultrasound transmitter and receiver system in relation to a ultrasound transducer of a high-intensity focused ultrasound system according to a further embodiment of the invention

In the embodiment shown in FIG. 13 the ultrasonic transducer elements 1102 still have the same relation as they did in FIGS. 11 and 12. However, in this embodiment there is no separate transmitter 1110. The ultrasound transducer elements 1102 function as the transmitter 1110 as shown in FIGS. 11 and 12. There are two receivers 1112 that are now located along the path of the therapeutic ultrasound 1104.

Figure 14:
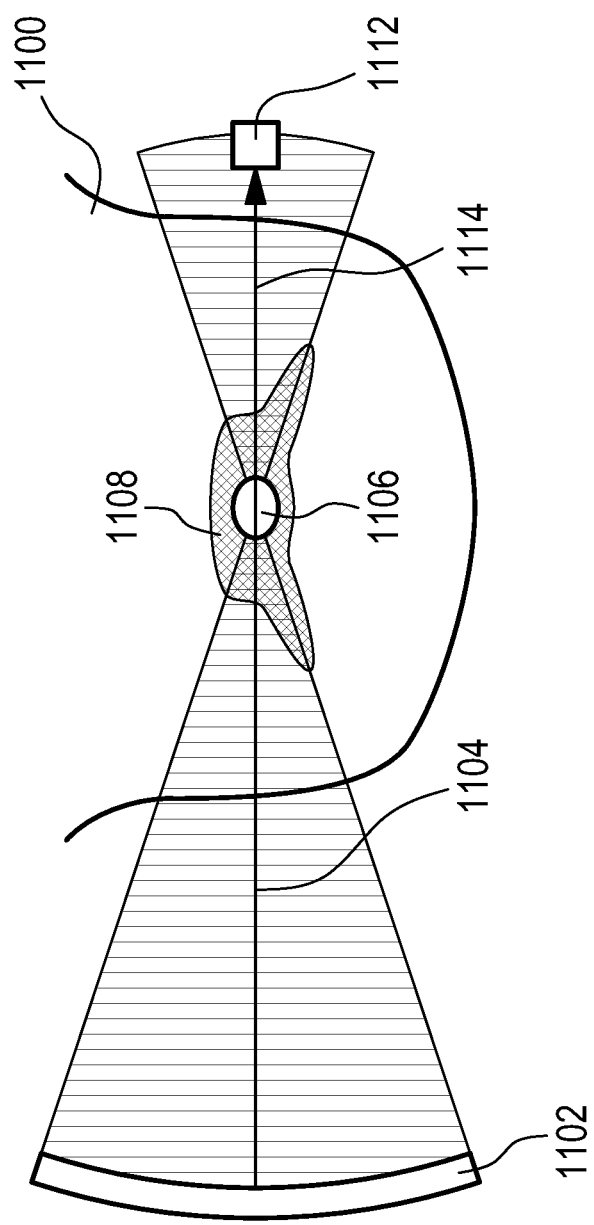
FIG. 14 illustrates the relative position of an ultrasound transmitter and receiver system in relation to a ultrasound transducer of a high-intensity focused ultrasound system according to a further embodiment of the invention.

In FIG. 14 the ultrasound transducer element is shown in a different configuration. In this embodiment the ultrasound transducer element 1102 is shown as being to the side of the subject 1100. The path of the therapeutic ultrasound 1104 is again focused to a sonication volume 1106 within the subject 1100. The heated region 1108 surrounds the sonication volume 1106. The therapeutic ultrasound 1104 leaves the region 1108 and travels to a receiver 1112. As with the embodiment shown in FIG. 13 there is no transmitter. The ultrasound transducer element 1102 functions as the transmitter 1110.

Figure 15:
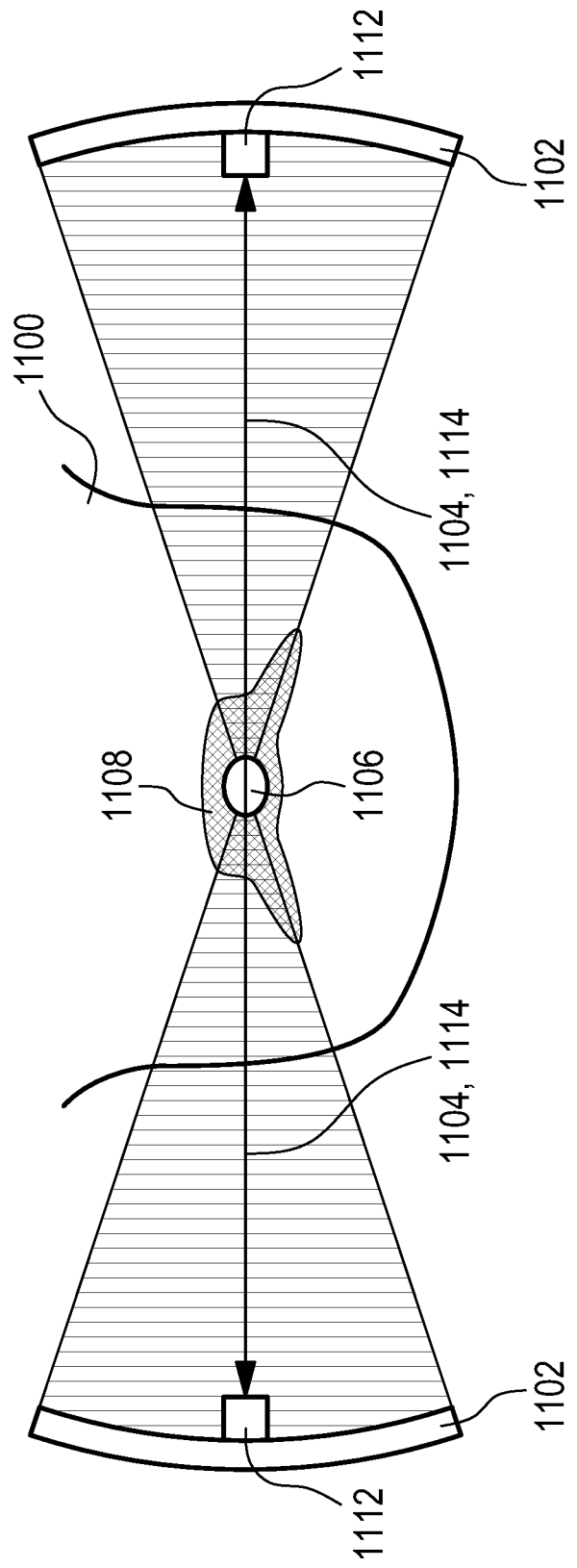
FIG. 15 illustrates the relative position of an ultrasound transmitter and receiver system in relation to a ultrasound transducer of a high-intensity focused ultrasound system according to a further embodiment of the invention.

The embodiment shown in FIG. 15 is similar to that of FIG. 14. In this embodiment there are two ultrasound transducer elements 1102. These are on adjacent sides of the subject 1100. The path of the therapeutic ultrasound 1104 is focused by both ultrasound transducer elements 1102 to the sonication volume 1106. Also in this embodiment the transmitter has been replaced by the ultrasound transducer elements 1102. The receiver 1112 is located on each of the ultrasound transducer elements 1102. The path through the subject 1114 is identical to the path of the therapeutic ultrasound 1104.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical apparatus comprising:
   a sonicating system configured to sonicate a target zone within a subject and comprising a tank filled with ultrasonic conducting liquid and including:
   an opening for receiving a portion of the subject including the target zone,
   a plurality of ultrasound transducer elements configured to generate ultrasonic energy and having controllable phases, and
   an ultrasound transmitter and receiver system configured to acquire data descriptive of a speed of the ultrasonic energy along at least two paths in the portion of the subject;
   an imaging system configured to obtain images of the at least two paths in the subject; and
   a processor configured to:
   segment the images to identify at least two tissue types,
   determine lengths of the at least two paths that correspond to distances traveled in the at least two tissue types by the ultrasonic energy, and
   calculate the speed of the ultrasonic energy in each of the at least two tissue types along the lengths of the at least two paths; and
   calculate phases for the plurality of transducer elements to sonicate the target zone based on the segmented images and the calculated speed of the ultrasonic energy in each of the at least two tissue types.

2. The medical apparatus of claim 1, wherein the data is acquired predominantly within a first plane through the tank, the first plane is below the opening, and the plurality of ultrasound transducer elements is positioned below a second plane that is below the first plane.

3. The medical apparatus of claim 2, wherein the ultrasound transducer elements are focused above the second plane.

4. The medical apparatus of claim 2, wherein the ultrasound transducer elements are focused below the second plane.

5. The medical apparatus of claim 2, wherein the at least two paths extend through the target zone.

6. The medical apparatus of claim 5, wherein the processors further configured to:
   determine a baseline of the speed of the ultrasonic energy along at least two baseline paths through the tank, the baseline and the speed of the ultrasonic energy are determined using ultrasonic amplitude measurements; and
   calculate an ultrasound attenuation value for each of the at least two tissue types in accordance with the ultrasonic amplitude measurements, the baseline, and the lengths of the at least two paths.

7. The medical apparatus of claim 1, further comprising a positioning system for positioning the subject and/or the ultrasound transmitter and receiver system, wherein the processor is further configured to:
   identify bone tissue in the segmented images, and
   position the subject and/or the ultrasound transmitter and receiver system such that the at least two paths are reflected off of the bone tissue and received by the receiver system.

8. The medical apparatus claim 1, wherein the processor is further configured to calculate ultrasound attenuation in each of the at least two tissue types in accordance with lengths of the at least two paths.

9. The medical apparatus of claim 1, wherein the processor is further configured to: generate ultrasound control signals in accordance with the phases of the plurality of transducer element to cause the sonicating system to sonicate the target zone.

10. The medical apparatus of claim 9, wherein the imaging system is a magnetic resonance imaging system for acquiring magnetic resonance from an imaging zone and the target zone is within the imaging zone, and the processor is further configured to:
- acquire magnetic resonance thermometry along a path generated from the ultrasound transducer elements to the target zone,
- calculate a plurality of temperature compensated transducer element phases in accordance with the segmented images and the magnetic resonance thermometry, and
- generate temperature corrected ultrasound control signals in accordance with the plurality of transducer element phases, and
- send the temperature corrected ultrasound control signals to the sonicating system.

11. The medical apparatus of claim 1, wherein the imaging system is selected from: a magnetic resonance imaging system, a computed tomography system, and a diagnostic ultrasound system.

12. A method of controlling a medical apparatus including:
- an imaging system to acquire images of at least two paths in a subject, and
- a sonicating system to sonicate a target zone within the subject, and comprising a tank filled with ultrasonic conducting liquid and having:
  - an opening for receiving a portion of the subject including the target zone,
  - a plurality of ultrasound transducer elements controlled to generate ultrasonic energy and having controllable phases,
  - an ultrasound transmitter and receiver system to acquire data descriptive of a speed of the ultrasonic energy along the at least two paths in the portion of the subject, the method comprising acts of:
- acquiring the images and the data descriptive of the speed of the ultrasonic energy;
- segmenting the images acquired from at least two tissue types;
- determining lengths of the at least two paths that correspond to the distances traveled in the at least two tissue types by the ultrasonic energy;
- calculating the speed of the ultrasonic energy in each of the at least two tissue types along the lengths of the at least two paths; and
- calculating phases for the plurality of transducer elements to sonicate the target zone based on the segmented images and the calculated speed of the ultrasonic energy in each of the at least two tissue types.

13. A non-transitory computer program product comprising machine executable instructions, which when executed by a processor perform a method of controlling a medical apparatus including:
- an imaging system to acquire images of at least two paths in a subject, and
- a sonicating system to sonicate a target zone within the subject, and comprising a tank filled with ultrasonic conducting liquid and having
  - an opening for receiving a portion of the subject including the target zone,
  - a plurality of ultrasound transducer elements controlled to generate ultrasonic energy and having controllable phases, and
  - an ultrasound transmitter and receiver system to acquire data descriptive of a speed of the ultrasonic energy along the at least two paths in a subject, the method comprising acts of:
- acquiring the images and the data descriptive of the speed of the ultrasonic energy;
- segmenting the images acquired from at least two tissue types;
- determining lengths of the at least two paths that correspond to the distances traveled in the at least two tissue types by the ultrasonic energy;
- calculating the speed of the ultrasonic energy in each of the at least two tissue types along the lengths of the at least two paths, and
- calculating phases for the plurality of transducer elements to sonicate the target zone based on the segmented images and the calculated speed of the ultrasonic energy in each of the at least two tissue types.

* * * * *